(12) United States Patent
Murthy et al.

(10) Patent No.: US 7,518,017 B2
(45) Date of Patent: Apr. 14, 2009

(54) FENICOL COMPOUNDS AND METHODS SYNTHESIZING 2-TRIFLUOROACETAMIDO-3-SUBSTITUTED PROPIOPHENONE COMPOUNDS

(75) Inventors: Yerramilli V. S. N. Murthy, Apex, NC (US); Felix Vattakunnel, Raleigh, NC (US)

(73) Assignee: Idexx Laboratories, Westbrook, ME (US)

( * ) Notice: Subject to any disclaimer, the term of this patent is extended or adjusted under 35 U.S.C. 154(b) by 109 days.

(21) Appl. No.: 11/700,073

(22) Filed: Jan. 31, 2007

(65) Prior Publication Data

US 2007/0197823 A1   Aug. 23, 2007

Related U.S. Application Data

(60) Provisional application No. 60/774,270, filed on Feb. 17, 2006.

(51) Int. Cl.
C07C 235/00     (2006.01)
A61K 31/16      (2006.01)

(52) U.S. Cl. ................... 564/123; 564/191; 564/192; 564/212; 564/213; 564/215; 514/625; 514/628

(58) Field of Classification Search .............. None
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,235,892 A | 11/1980 | Nagabhushan |
| 4,311,857 A | 1/1982 | Nagabhushan |
| 4,582,918 A | 4/1986 | Nagabhushan et al. |
| 4,677,214 A | 6/1987 | Nagabhushan et al. |
| 4,743,700 A | 5/1988 | Jommi et al. |
| 4,876,352 A | 10/1989 | Schumacher et al. |
| 4,973,750 A | 11/1990 | Nagabhushan et al. |
| 5,059,595 A | 10/1991 | Le Grazie |
| 5,073,543 A | 12/1991 | Marshall et al. |
| 5,105,009 A | 4/1992 | Jommi et al. |
| 5,120,548 A | 6/1992 | McClelland et al. |
| 5,153,328 A | 10/1992 | Jommi et al. |
| 5,202,484 A | 4/1993 | Villa et al. |
| 5,227,494 A | 7/1993 | Schumacher et al. |
| 5,243,056 A | 9/1993 | Jommi et al. |
| 5,284,966 A | 2/1994 | Villa et al. |
| 5,332,835 A | 7/1994 | Jommi et al. |
| 5,346,828 A | 9/1994 | Stirling et al. |
| 5,352,832 A | 10/1994 | Wu et al. |
| 5,354,556 A | 10/1994 | Sparks et al. |
| 5,382,673 A | 1/1995 | Clark et al. |
| 5,401,852 A | 3/1995 | Villa et al. |
| 5,556,829 A | 9/1996 | Camaggi et al. |
| 5,567,844 A | 10/1996 | Jommi et al. |
| 5,591,767 A | 1/1997 | Mohr et al. |
| 5,621,111 A | 4/1997 | Lui et al. |
| 5,639,476 A | 6/1997 | Oshlack et al. |
| 5,663,361 A | 9/1997 | Towson et al. |
| 5,674,533 A | 10/1997 | Santus et al. |
| 5,733,566 A | 3/1998 | Lewis |
| 5,789,599 A | 8/1998 | Davis et al. |
| 5,908,937 A | 6/1999 | Jommi et al. |
| 6,080,886 A | 6/2000 | Lal et al. |
| 6,207,860 B1 | 3/2001 | Lal et al. |
| 7,041,670 B2 | 5/2006 | Boojamra et al. |
| 2003/0216447 A1 | 11/2003 | Kohan et al. |
| 2003/0220302 A1 | 11/2003 | Kohan et al. |
| 2005/0075506 A1 | 4/2005 | Handa et al. |
| 2005/0159604 A1 | 7/2005 | Zhang |

FOREIGN PATENT DOCUMENTS

JP          62 209047 A     9/1987

OTHER PUBLICATIONS

Osorio-Olivares M., et al., Tetrahedron Asymmetry, Pergamon Oxford, GB, vol. 14, No. 11, Jun. 6, 2003, 1473-77.
Muller et al., Journal Fur Praktische Chemie, vol. 315, No. 6 (1973) 1045-1056 (with English abstract).
Fuji, I. et al., J. Amer. Chem. Soc., vol. 117 (1995), 6199-6209.
The Merck Index (2006) p. 1599, col. 2, compound 9301.
Norlander et al., J. Org. Chem., vol. 50 (1985), 3481-3484.
European Search Report dated Sep. 5, 2008.
*Antibiotics*, F. E. Hahn, Ed. Gottlieb and Shaw Springer-Verlag, New York (1967), p. 308.
*Antibiotics and Chemotherapy*, F.E. Hahn et al., 6, No. 9, 531 (1959).
L. Cima and A. Ilecto, Il Farmaco, Ed. Sc.12, No. 6, 535 (1957).
*Jap. J. Microbiol*, S. Mitsuhasi et al., 13, No. 2, 177-80 (1969).
*Jap. J. Microbiology*, M. Kono et al., 15 (3), 219-27 (1971).

*Primary Examiner*—Brian J Davis
(74) *Attorney, Agent, or Firm*—Townsend and Townsend and Crew, LLP.

(57) ABSTRACT

Methods of preparing compounds of formula (I):

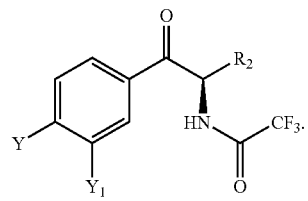

wherein Y, $Y_1$, and $R_2$ are defined herein; methods of making D-(threo)-1-aryl-2-acylamido-1-propanol compounds, D-(threo)-1-aryl-2-acylamido-3-fluoro-1-propanol compounds, and D-(threo)-1-aryl-2-acylamido-3-hydroxy-1-propanol compounds (collectively, "fenicol compounds") from the compound of formula (I); and new fenicol compounds, which can be made using the method.

38 Claims, No Drawings

US 7,518,017 B2

FENICOL COMPOUNDS AND METHODS SYNTHESIZING 2-TRIFLUOROACETAMIDO-3-SUBSTITUTED PROPIOPHENONE COMPOUNDS

CROSS REFERENCE TO RELATED APPLICATIONS

This application claims the benefit of U.S. provisional application Ser. No. 60/774,270, filed Feb. 17, 2006, the contents of which are expressly incorporated herein.

FIELD OF THE INVENTION

The present invention is directed to methods of preparing 2-trifluoroacetamido-3-substituted propiophenone compounds and methods of preparing 1-aryl-2-acylamido-1-propanol compounds, 1-aryl-2-acylamido-3-fluoro-1-propanol compounds, and 1-aryl-2-acylamido-3-hydroxy-1-propanol compounds (collectively, "fenicol compounds") from the 2-trifluoroacetamido-3-substituted propiophenone compounds.

BACKGROUND OF THE INVENTION

Bacterial infections, especially bacterial infections of the respiratory tract, are a major problem for production animals such as cattle, pigs, sheep, and other livestock. Bacterial infections are also a common problem with companion animals such as cats, dogs, and horses. Bacterial infections are typically treated using antibiotics.

A class of broad spectrum antibiotics classified as D-(threo)-1-p-substituted phenyl-2-halogenoacetylamido-1,3-propanediols are known in the art. This class of antibiotics includes chloramphenicol(D-(threo)-1-p-nitrophenyl-2-dichloroacetamido-1,3-propanediol), thiamphenicol(D-(threo)-1-p-methylsulfonylphenyl-2-dichloroacetamido-1,3-propanediol), fluorthiamphenicol(D-(threo)-1-p-methylsulfonylphenyl-2-difluoroacetamido-1,3-propanediol) and tevenel(D-(threo)-1-p-aminosulfonylphenyl-2-dichloroacetamido-1,3-propanediol) (See, U.S. Pat. No. 4,235,892 to Nagabhushan). Replacing the primary hydroxyl group at C-3 of chloramphenicol by chlorine or bromine, however, destroys the biological activity thereof (F. E. Hahn, *Antibiotics*, Ed. Gottlieb and Shaw, Springer-Verlag, New York, (1967), p. 308; F. E. Hahn et al, *Antibiotics and Chemotherapy*, 6, No. 9, 531 (1956); L. Cima and A. Ilecto, II Farmaco, Ed. Sc. 12, No. 6, 535 (1957); S. Mitsuhasi et al, *Jap. J. Microbial.* 13, No. 2, 177-80 (1969); M. Kono et al, *Jap. J. Microbiology* 15 (3), 219-27 (1971); and U.S. Pat. No. 4,235,892 to Nagabhushan).

U.S. Pat. Nos. 4,235,892; 4,311,857; and 4,677,214 disclose D-(threo)-1-aryl-2-acylamido-3-fluoro-1-propanol compounds that are allegedly useful as antibiotics. Florfenicol, [(R-(R*,S*)]-2,2-dichloro-N-[1-fluoromethyl)-2-hydroxy-2-[4-(methylsulfonyl)phenyl]ethyl]acetamide or D-threo-2,2-dichloro-N-[1-(fluoromethyl)-2-hydroxy-2-[4-methylsulfonyl) phenyl]ethyl]-acetamide), commercially available from Schering-Plough Animal Health, New Jersey as NUFLOR®, is an example of an antibiotic in this class of compounds.

United States published patent application no. US 2003/0216447 and United States published patent application no. US 2003/0220302 each disclose compositions comprising flunixin and a florfenicol or florfenicol-like compound that are allegedly useful for treating microbial infections in animals.

International publication WO 03/077828 discloses fluorfenicol 1-type antibiotics that allegedly exhibit antimicrobial activity.

US 2005/0075506 discloses a process for preparing florfenicol that involves forming an oxazolidine compound from a 1-phenyl-3-hydroxy-2-amino-1-propanol compound and fluorinating the oxazolidine compound.

U.S. Pat. Nos. 4,743,700; 5,332,835; 5,153,328; and 5,567,844 each disclose a method for replacing the fluorine of the primary hydroxy group of a 1-phenyl-2-amino-1,3-propanediol compounds by protecting the secondary hydroxy group and the amino group and fluorinating with inorganic fluoride in polyglycol. The secondary hydroxy group and the amino group can be protected as an oxazoline.

U.S. Pat. No. 5,352,832 discloses a stereospecific process for preparing florfenicol, thiamphenicol, and chloramphenicol having the correct relative and absolute stereochemistry from achiral trans-cinnamic acid derivatives.

U.S. published application no. US 2005/0075506 discloses a process to prepare florfenicol from (1R,2R)-2-amino-1-[(4-methylsulfonyl)phenyl]-1,3,propanediol that involves forming an oxazolidine intermediate.

U.S. Pat. No. 5,663,361 discloses a method for making an ozazoline intermediate useful for preparing florfenicol.

U.S. Pat. No. 5,382,673 discloses a method for making florfenicol that involves formation of an ozazoline intermediate.

U.S. Pat. Nos. 5,105,009; 5,908,937; and 5,243,056 each disclose a method for preparing 1-(phenyl)-1-hydroxy-2-amino-3-fluoro-propane derivatives via an oxazolidine intermediate.

U.S. Pat. No. 5,789,599 discloses N-sulfinyl-2-carboxyaziridine compounds and the synthesis of florfenicol, thiamphenicol, and chloramphenicol from the N-sulfinyl-2-carboxyaziridine compounds.

U.S. Pat. No. 4,582,918 discloses the preparation of cis-1-aryl-2-(fluoromethyl)oxiranes and there use in preparing (threo)-1-aryl-2-acylamido-3-fluoro-1-propanols.

U.S. Pat. No. 5,556,829 discloses amide compounds that are useful in agriculture as herbicides in the defense of useful crops from weeds.

There is a need in the art, however, for improved methods of preparing this class of antibiotics, i.e., D-(threo)-1-aryl-2-acylamido-1-propanol compounds, D-(threo)-1-aryl-2-acylamido-3-fluoro-1-propanol compounds, and D-(threo)-1-aryl-2-acylamido-3-hydroxy-1-propanol compounds. The present invention addresses this need.

Citation of any reference in this section of this application is not to be construed that such reference is prior art to the present application.

SUMMARY OF THE INVENTION

The invention is directed to a method of synthesizing a 2-trifluoroacetamido-3-substituted propiophenone compounds of formula (I):

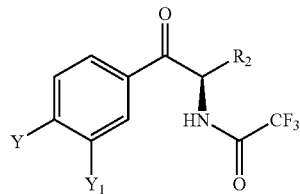

comprising contacting a compound of formula (II):

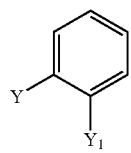

with a compound of formula (III):

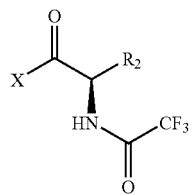

wherein:
R$_2$ is —CH$_3$, —CH$_2$OH, —CH$_2$OP, or —CH$_2$F;
each Y and Y$_1$ is independently —H; —SO$_2$R$_1$; —S(O)R$_1$—SR$_1$; —S(O)NH$_2$; —SO$_2$NH$_2$; —S(O)NHR$_1$; —S(O)NHR$_1$; —S(O)N(R$_1$)$_2$; —S(O)N(R$_1$)$_2$; —C(O)R$_1$; —C(O)OR$_1$; —OC(O)R$_1$; —OR$_1$; —R$_1$; —CN; halogen; —NO$_2$; —NH$_2$; —NHR$_1$; —NH(R$_1$)$_2$; —C(O)NH$_2$; —C(O)NHR$_1$; —C(O)N(R$_1$)$_2$; phenyl; or phenyl substituted with halogen; —NO$_2$, —SO$_2$R$_1$, —OR$_1$, or —R$_1$;
each R$_1$ is independently a C$_1$-C$_4$ hydrocarbon group;
X is a halogen; and
P is a hydroxyl protecting group.

The invention further relates to a method of synthesizing a fenicol compound of formula (VI):

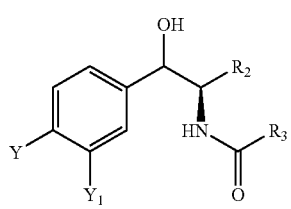

wherein Y, Y$_1$, and R$_2$ are defined above,
R$_3$ is a —C$_1$-C$_4$ hydrocarbon group, —CH$_2$F, —CHF$_2$, —CF$_3$, —CH$_2$Cl, —CHCl$_2$, —CCl$_3$, —CH$_2$Br, —CHBr$_2$, —CBr$_3$, —CH$_2$I, —CHI$_2$, —CI$_3$, —CH$_2$CN, —CH$_2$N$_3$, —CH$_2$SO$_2$CH$_3$, —CZ$_2$CZ$_3$, —CH(CH$_3$)(CF$_3$), —CH(OH)(CH$_3$), —CH(CF$_3$)$_2$, —CH(CF$_3$)Z, and —CH(CF$_3$)OH; and
each Z is independently a hydrogen or halogen,
comprising the steps of:
(i) contacting a compound of formula (III):

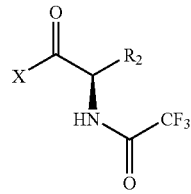

wherein:
X is a halide;
with a compound of formula (II):

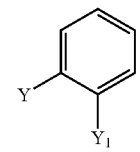

to provide a compound of formula (I):

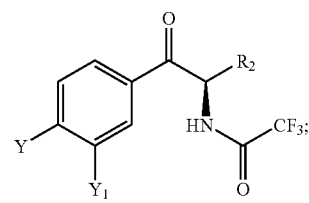

(ii) contacting the compound of formula (I) with a reducing agent to provide a compound of formula (VII):

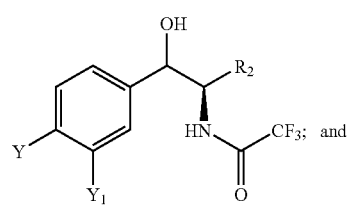

(ii) converting the compound of formula (VII) to a compound of formula (VIII):

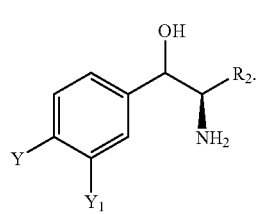

The invention further relates to a method of synthesizing a fenicol compound of formula (VI):

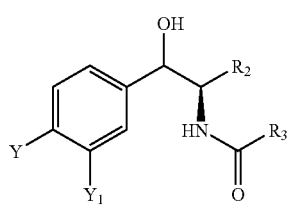
(VI)

wherein Y, $Y_1$, $R_2$, and $R_3$ are defined above comprising the step of converting an amino acid of formula (V):

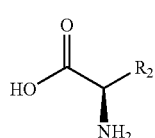
(V)

to a N-trifluoroacetylated amino acid of formula (IV):

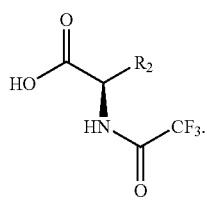
(IV)

The invention further relates to a method of synthesizing a fenicol compound of formula (VI):

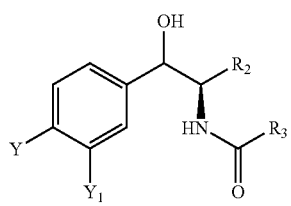
(VI)

wherein Y, $Y_1$, $R_2$, and $R_3$ are defined above comprising the step of contacting a compound of formula (III):

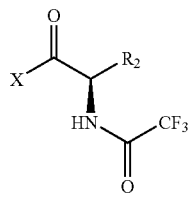
(III)

wherein X is a halide;

with a compound of formula (II):

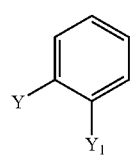
(II)

to provide a compound of formula (I):

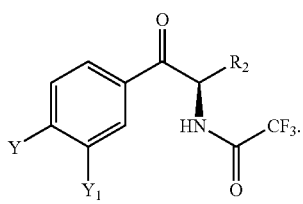
(I)

The invention further relates to a method of synthesizing a fenicol compound of formula (VI):

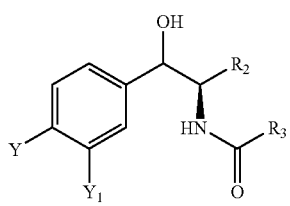
(VI)

wherein Y, Y$_1$, and R$_2$, R$_3$ are defined above comprising the step of contacting a compound of formula (I):

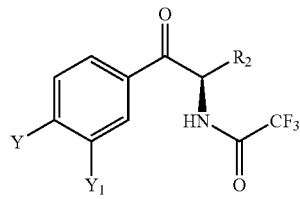
(I)

with a reducing agent to provide a compound of formula (VII):

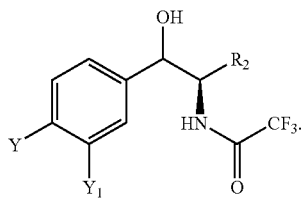
(VII)

The invention further relates to a method of synthesizing a fenicol compound of formula (VI):

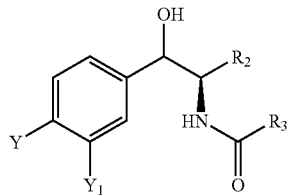
(VI)

wherein Y, Y$_1$, R$_2$, and R$_3$ are defined above, comprising the steps:

(i) of converting a compound of formula (VII):

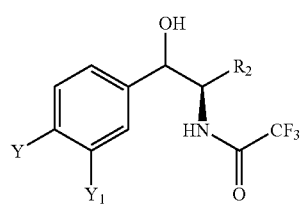
(VII)

to a compound of formula (VIII):

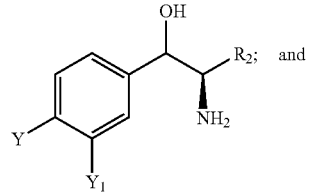
(VIII)

(ii) converting the compound of formula (VIII) to the fenicol compound of formula (VI).

The invention further relates to a compound of formula (I):

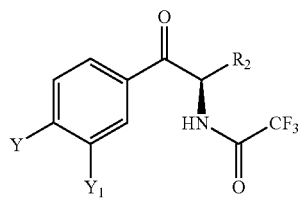
(I)

wherein:

R$_2$ is —CH$_3$, —CH$_2$OH, —CH$_2$OP, or —CH$_2$F;

each Y and Y$_1$ is independently —H; —SO$_2$R$_1$; —SOR$_1$—SR$_1$; —SONH$_2$; —SO$_2$NH$_2$; —SONHR$_1$; —SONHR$_1$; —SON(R$_1$)$_2$; —SON(R$_1$)$_2$; —COR$_1$; —COOR$_1$; —OCR$_1$; —OR$_1$; —R$_1$; —CN; halogen; —NO$_2$; —NH$_2$; —NHR$_1$; —NH(R$_1$)$_2$; —CONH$_2$; —CONHR$_1$; —CON(R$_1$)$_2$; phenyl; or phenyl substituted with halogen; —NO$_2$, —SO$_2$R$_1$, —OR$_1$, or —R$_1$;

each R$_1$ is independently a C$_1$-C$_4$ hydrocarbon group; and

P is a hydroxyl protecting group.

The invention further relates to a compound of formula (VIa1):

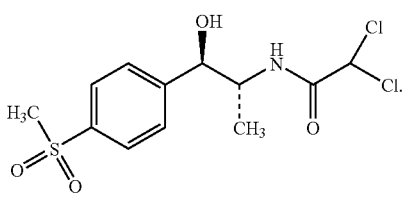
(VIa1)

The invention further relates to a pharmaceutical composition comprising the compound of formula (VIa1) and a pharmaceutically acceptable excipient and to methods of treating or preventing a condition in an animal comprising administering to the animal the pharmaceutical composition.

DETAILED DESCRIPTION OF THE INVENTION

The invention is directed to a method of synthesizing 2-trifluoroacetamido-3-substituted propiophenone compounds, i.e., compounds of formula (I)

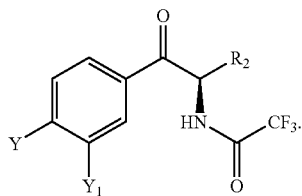

(I)

The compounds of formula (I) are useful for the preparing fenicol compounds. Accordingly, the invention further relates to a method of preparing fenicol compounds from the compounds of formula (I). In one embodiment, the compounds of formula (I) used to prepare the fenicol compound are obtained according to the method of the invention.

DEFINITIONS

The term "halo," and "halogen," as used herein, means chloride, bromide, iodide, and fluoride.

The phrase "fenicol compound," as used herein, means a compound of general formula (VI):

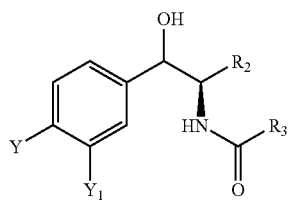

(VI)

wherein $R_2$ is —$CH_3$, —$CH_2OH$, —$CH_2OP$, or —$CH_2F$;

each Y and $Y_1$ is independently —H; —$SO_2R_1$; —S(O)$R_1$—$SR_1$; —S(O)$NH_2$; —$SO_2NH_2$; —S(O)$NHR_1$; —S(O)$NHR_1$; —S(O)$N(R_1)_2$; —S(O)$N(R_1)_2$; —C(O)$R_1$; —C(O)$OR_1$; —OC(O)$R_1$; —$OR_1$; —$R_1$; —CN; halogen; —$NO_2$; —$NH_2$; —$NHR_1$; —$NH(R_1)_2$; —C(O)$NH_2$; —C(O)$NHR_1$; —C(O)$N(R_1)_2$; phenyl; or phenyl substituted with halogen; —$NO_2$, —$SO_2R_1$, —$OR_1$, or —$R_1$;

each $R_1$ is independently a $C_1$-$C_4$ hydrocarbon group;

P is a hydroxyl protecting group;

$R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —$CH(OH)(CH_3)$, —$CH(CF_3)_2$, —$CH(CF_3)Z$, and —$CH(CF_3)OH$; and each Z is independently a hydrogen or halogen.

The phrase "substantially free," as used herein, means less than about 5 percent by weight. For example, the phrase "diasteriomer (VIa) substantially free of diasteriomer (VIb)" means a composition containing a compound of formula (VIa) wherein the amount of diasteriomer (VIb) in the composition is less than about 5 percent by weight of the combined amount of (VIa) and (VIb).

The phrase "$C_1$-$C_4$ hydrocarbon group," as used herein, means a straight chain, saturated or unsaturated, cyclic or acylic hydrocarbon chain. Representative —$C_1$-$C_4$ hydrocarbon groups include, but are not limited to, methyl, ethyl, n-propyl, iso-propyl, n-butyl, iso-butyl, sec-butyl, cyclopropyl, cyclobutyl, ethylene, 1-propylene, 2-propylene, 1-butylene, and 2-butylene.

The phrase "$C_1$-$C_{18}$ hydrocarbon group" means a straight or branched, saturated or unsaturated, cyclic or non-cyclic, aromatic or non-aromatic hydrocarbon having from 1 to 18 carbon atoms. Accordingly, the phrase "an acyl group of formula —C(O)—$R_4$, wherein $R_4$ is a $C_1$ to $C_{18}$ hydrocarbon group that may optionally be substituted with a —$NH_2$ or —COOH" means $R_4$ of the acyl group of formula —C(O)—$R_4$ is a straight or branched, saturated or unsaturated, cyclic or non-cyclic, aromatic or non-aromatic hydrocarbon having from 1 to 18 carbon atoms that may optionally be substituted with a —$NH_2$ or —COOH. Representative acyl group of formula —C(O)—$R_4$, wherein $R_4$ is an unsubstituted $C_1$ to $C_{18}$ hydrocarbon group include, but are not limited to, acetyl, propionyl, butanoyl, hexanoyl, caproyl, lauroyl, myristoyl, palmitoyl, stearoyl, palmioleoyl, oleoyl, linoleoyl, linolenoyl, and benzoyl. Representative acyl groups of formula —C(O)—$R_4$, wherein $R_4$ is a $C_1$ to $C_{18}$ hydrocarbon group that is substituted with a —COOH, include but are not limited to, oxaloyl, malonoyl, succinoyl, glutamoyl, adipoyl, and pimeloyl. Representative acyl groups of formula —C(O)—$R_4$, wherein $R_4$ is a $C_1$ to $C_{18}$ hydrocarbon group that is substituted with a —$NH_2$, include but are not limited to, acyl groups derived from amino acids such as tyrosine, alanine, threonine, serine, hydroxyproline, proline, phenylalanine, leucine, valine, and glycine.

The phrase "hydroxyl protecting group," as used herein, means a group that can replace the hydrogen of a hydroxyl, i.e., the hydrogen of an —OH group, and then be subsequently removed and replaced by a hydrogen to reform the hydroxyl group. The hydroxyl protecting group prevents the hydroxyl from reacting under a given set of conditions, which typically are necessary to perform a reaction at another part of a molecule. After reaction at the other part of the molecule, the hydroxyl protecting group can be removed to provide the hydroxyl group. Suitable hydroxyl protecting groups, P, include those described in T. W. Greene, Protective Groups in Organic Synthesis, John Wiley-Interscience Publication, New York, (1981). Representative protecting groups include, but are not limited to, esters and ethers. Preferably, the hydroxyl group is protected as an ester. In one embodiment, the hydroxyl group is protected as an acetate ester.

The phrase "treating," "treatment of," and the like, as used herein, include the amelioration or cessation of a specified condition.

The phrase "preventing," "prevention of," and the like, as used herein, include the avoidance of the onset of a condition.

The term "condition," as used herein means an interruption, cessation, or disorder of a bodily function, system, or organ.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human.

The term "effective amount," as used herein, means an amount sufficient to treat or prevent a condition in an animal.

The term "about," as used herein to describe a range of values, applies to both the upper limit and the lower limit of the range. For example, the phrase "the concentration of the compound of formula (II) in the solvent ranges from about 0.01 M to 5 M" has the same meaning as "the concentration of the compound of formula (II) in the solvent ranges from about 0.01 M to about 5 M."

Synthesis of the 2-Trifluoroacetamido-3-Substituted Propiophenone Compounds

The present invention is directed to a method of preparing compounds of formula (I):

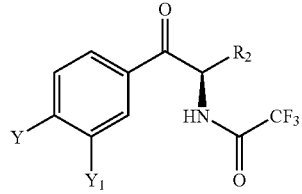

wherein:

$R_2$ is —$CH_3$, —$CH_2OH$, —$CH_2OP$, or —$CH_2F$;

each Y and $Y_1$ is independently —H; —$SO_2R_1$; —S(O)$R_1$—$SR_1$; —S(O)$NH_2$; —$SO_2NH_2$; —S(O)$NHR_1$; —S(O)$NHR_1$; —S(O)$N(R_1)_2$; —S(O)$N(R_1)_2$; —C(O)$R_1$; —C(O)$OR_1$; —OC(O)$R_1$; —$OR_1$; —$R_1$; —CN; halogen; —$NO_2$; —$NH_2$; —$NHR_1$; —$NH(R_1)_2$; —C(O)$NH_2$; —C(O)$NHR_1$; —C(O)$N(R_1)_2$; phenyl; or phenyl substituted with halogen; —$NO_2$, —$SO_2R_1$, —$OR_1$, or —$R_1$;

each $R_1$ is independently a $C_1$-$C_4$ hydrocarbon group; and

P is a hydroxyl protecting group.

The process comprises contacting an aromatic compound of formula (II):

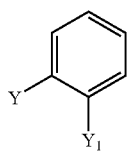

wherein Y and $Y_1$ have the meaning described above;

with an acid halide of an N-trifluoracetylated amino acid of formula (III):

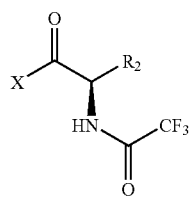

wherein $R_2$ has the meaning described above and X is a halogen.

The general reaction is depicted below:

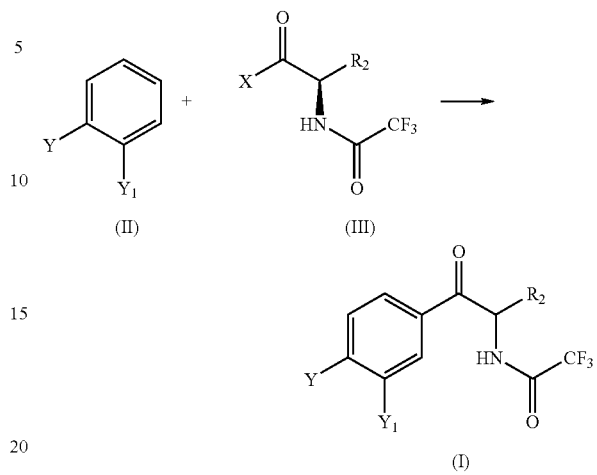

wherein $R_2$, X, Y, and $Y_1$ have the meaning described above.

One of ordinary skill in the art will readily recognize, however, that the reaction between the compound of formula (II) and the acid halide of N-trifluoracetylated amino acid of formula (III) is not limited to amino acids that are N-protected with a trifluoroacetyl group. Indeed, the acid chloride of any N-protected amino acid could be used in the methods of the invention. The general structure for an N-protected amino acid is:

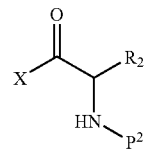

wherein $R_2$ and X have the meaning described above and $P^2$ is a N-protecting groups. One of ordinary skill in the art would readily know suitable N-protecting groups, $P^2$. Suitable N-protecting groups useful in the methods of the invention include, but are not limited to, those described in T. W. Greene, Protective Groups in Organic Synthesis, John Wiley-Interscience Publication, New York, (1981). The acid halide of an N-trifluoracetylated amino acid, i.e., an N-protected amino acid wherein $P^2$ is —C(O)$CF_3$, is simply a preferred acid halide of an N-protected amino acid.

In one embodiment, the compound of formula (II) is contacted with the compound of formula (III) in a solvent. Preferably, at least one of the compound of formula (II) or the compound of formula (III) are dissolved in the solvent. More preferably, both the compound of formula (II) and the compound of formula (III) are dissolved in the solvent. Suitable solvents for use in the methods of the invention include, but are not limited to, inert organic solvents such as nitrobenzene, nitromethane, dichloromethane, and chloroform. One of ordinary skill in the art would readily recognize solvents that are useful for conducting a Friedel Crafts acylation.

One of ordinary skill in the art would readily be able to determine a suitable concentration of the compound of formula (II) in the solvent. Typically, the concentration of the compound of formula (II) in the solvent ranges from about 0.01 M to 5 M. In one embodiment, the concentration of the compound of formula (II) in the solvent ranges from about 0.05 M to 2.5 M. In one embodiment, the concentration of the compound of formula (II) in the solvent ranges from about 0.1 M to 1 M.

The ratio of the compound of formula (II) to the compound of formula (III) generally ranges from about 1:1 to 5:1. In one embodiment, the ratio of the compound of formula (II) to the compound of formula (III) ranges from about 1.25:1 to 3.5:1. In one embodiment, the ratio of the compound of formula (II) to the compound of formula (III) ranges from about 2:1 to 3:1. In one embodiment, the ratio of the compound of formula (II) to the compound of formula (III) generally is greater than about 1:1. In one embodiment, the ratio of the compound of formula (II) to the compound of formula (III) generally is greater than about 2:1. In one embodiment, the ratio of the compound of formula (II) to the compound of formula (III) generally is greater than about 3:1. In one embodiment, the ratio of the compound of formula (II) to the compound of formula (III) generally is greater than about 5:1.

In one embodiment, the compound of formula (II) is contacted with the compound of formula (III) under neat conditions, i.e., the compound of formula (II) is present in an excess and also acts as the solvent for the reaction. Typically, the compound of formula (II) is present in at least a 5 molar excess relative to the compound of formula (III). In one embodiment, the compound of formula (II) is present in at least a 10 molar excess relative to the compound of formula (III). In one embodiment, the compound of formula (II) is present in at least a 15 molar excess relative to the compound of formula (III). In one embodiment, the compound of formula (II) is present in at least a 20 molar excess relative to the compound of formula (III). In one embodiment, the compound of formula (II) is present in at least a 30 molar excess relative to the compound of formula (III).

The compound of formula (II) and the compound of formula (III) are contacted for an amount of time sufficient to allow the compound of formula (II) and the compound of formula (III) to react and provide the compound of formula (I). The progress of the reaction can be monitored using typical analytical methods well known to those skilled in the art including, but not limited to, gas chromatography (GC), high performance liquid chromatography (HPLC), thin-layer chromatography (TLC), $^1$H nuclear magnetic resonance spectroscopy ($^1$H-NMR), and $^{13}$C nuclear magnetic resonance spectroscopy ($^{13}$C-NMR).

Typically, the compound of formula (II) and the compound of formula (III) are contacted at a temperature of between about −15° C. and 35° C. In one embodiment, the compound of formula (II) and the compound of formula (III) are contacted at a temperature of between about −10° C. and 25° C. In one embodiment, the compound of formula (II) and the compound of formula (III) are contacted at a temperature of between about −5° C. and 10° C. In one embodiment, the compound of formula (II) and the compound of formula (III) are contacted at a temperature of about 0° C. In one embodiment, after the compound of formula (II) and the compound of formula (III) are contacted, the temperature of the resulting reaction mixture is increased. In one embodiment, the temperature is increased by about 30° C. In one embodiment, the temperature is increased by about 20° C. In one embodiment, the temperature is increased by about 10° C. In one embodiment, the temperature is increased to about 25° C.

One of ordinary skill in the art will readily recognize that different compounds of formula (II), depending on the substituents Y and $Y_1$, will react with the compound of formula (III) at different rates. As described above, however, the progress of the reaction can be monitored using typical analytical methods well known to those skilled in the art. Generally, however, the reaction of the compound of formula (II) and the compound of formula (III) is allowed to proceed for more than 2 h. In one embodiment, the reaction is allowed to proceed for more than 5 h. In one embodiment, the reaction is allowed to proceed for more than 10 h. In one embodiment, the reaction is allowed to proceed for more than 15 h.

In a particular embodiment, the compound of formula (II) and the compound of formula (III) are contacted at a temperature of about 0° C. and, after the compound of formula (II) and the compound of formula (III) are contacted, the temperature of the resulting reaction mixture is increased to about 25° C. and the warmed reaction mixture allowed to stir between about 10 and 15 h.

In one embodiment, the compound of formula (II) is contacted with the compound of formula (III) in the presence of a Friedel-Crafts catalyst. Friedel-Crafts catalysts are well known to those skilled in the art. Any Friedel-Crafts catalyst can be used in the methods of the invention. Representative Friedel-Crafts catalysts include, but are not limited to, $AlCl_3$, $AlBr_3$, $BF_3$, $BCl_3$, $GaCl_3$, $FeCl_3$, $SbCl_5$, $ZrCl_4$, $SnCl_4$, $SbCl_3$, and $ZnCl_2$. The catalyst is generally present in an amount ranging from about 0.1 molar equivalents to 5 molar equivalents relative to the compound of formula (III). In one embodiment, the catalyst is present in an amount ranging from about 0.1 molar equivalents to 3 molar equivalents relative to the compound of formula (III). In one embodiment, the catalyst is present in an amount ranging from about 0.1 molar equivalents to 1 molar equivalents relative to the compound of formula (III). In one embodiment, the catalyst is present in an amount ranging from about 1 molar equivalents to 3 molar equivalents relative to the compound of formula (III).

After the reaction is complete, the compound of formula (I) can be isolated and purified using methods well known to those skilled in the art including, but not limited to, TLC, column chromatography, preparative HPLC, extraction, and recrystallization.

The aromatic compounds of formula (II) are commercially available or can be prepared using methods well known to those of ordinary skill in the art.

In one embodiment, in the compound of formula (II) Y is —$NO_2$ and $Y_1$ is —H.

In one embodiment, in the compound of formula (II) Y is —$SO_2CH_3$ and $Y_1$ is —H.

In one embodiment, in the compound of formula (II) Y is —$SO_2NH_2$ and $Y_1$ is —H.

In one embodiment, in the compound of formula (III) X is —Cl.

In one embodiment, in the compound of formula (III) X is —Br.

In one embodiment, in the compound of formula (III) X is —I.

In one embodiment, in the compound of formula (III) X is —F.

In one embodiment, in the compound of formula (III) $R_2$ is —$CH_3$.

In one embodiment, in the compound of formula (III) $R_2$ is —$CH_2OH$.

In one embodiment, in the compound of formula (III) $R_2$ is —$CH_2OP$.

In one embodiment, in the compound of formula (III) $R_2$ is —$CH_2F$.

In one embodiment, in the compound of formula (III) $R_2$ is —$CH_3$ and X is —Cl.

In one embodiment, in the compound of formula (III) $R_2$ is —$CH_2OH$ and X is —Cl.

In one embodiment, in the compound of formula (III) $R_2$ is —$CH_2OP$ and X is Cl.

In one embodiment, in the compound of formula (III) $R_2$ is —$CH_2F$ and X is Cl.

One of ordinary skill in the art will readily recognize that there are several available positions on the compound of formula (II) that can be acylated by the compound of formula (III) and that the position that is most reactive is determined by the substitutents Y and $Y_1$. Thus, the reaction can form more than one compound, i.e., a mixture of compounds resulting from different positions of the compound of formula (II) being acylated. These mixtures, however, can be separated by methods well known to those of ordinary skill in the art including, but not limited to, crystallization, distillation, column chromatography, thin layer chromatography, and HPLC. One of ordinary skill in the art would also readily recognize that it may be necessary to modify the compound of formula (II), for example, with a protecting group, before the compound of formula (II) is reacted with the compound of formula (III) to assure that the proper position on the compound of formula (II) is acylated. Methods for acylating compounds of formula (II) are well within the skill of one of ordinary skill in the art.

In one embodiment, Y is —$NO_2$ and $Y_1$ is —H in the compound of formula (II) and $R_2$ in the compound of formula (III) is —$CH_3$.

In one embodiment, Y is —$NO_2$ and $Y_1$ is —H in the compound of formula (II) and $R_2$ in the compound of formula (III) is —$CH_2OH$.

In one embodiment, Y is —$NO_2$ and $Y_1$ is —H in the compound of formula (II) and $R_2$ in the compound of formula (III) is —$CH_2OP$.

In one embodiment, Y is —$NO_2$ and $Y_1$ is —H in the compound of formula (II) and $R_2$ in the compound of formula (III) is —$CH_2F$.

In one embodiment, Y is —$SO_2CH_3$ and $Y_1$ is —H in the compound of formula (II) and $R_2$ in the compound of formula (III) is —$CH_3$.

In one embodiment, Y is —$SO_2CH_3$ and $Y_1$ is —H in the compound of formula (II) and $R_2$ in the compound of formula (III) is —$CH_2OH$.

In one embodiment, Y is —$SO_2CH_3$ and $Y_1$ is —H in the compound of formula (II) and $R_2$ in the compound of formula (III) is —$CH_2OP$.

In one embodiment, Y is —$SO_2CH_3$ and $Y_1$ is —H in the compound of formula (II) and $R_2$ in the compound of formula (III) is —$CH_2F$.

In one embodiment, Y is —$SO_2NH_2$ and $Y_1$ is —H in the compound of formula (II) and $R_2$ in the compound of formula (III) is —$CH_3$.

In one embodiment, Y is —$SO_2NH_2$ and $Y_1$ is —H in the compound of formula (II) and $R_2$ in the compound of formula (III) is —$CH_2OH$.

In one embodiment, Y is —$SO_2NH_2$ and $Y_1$ is —H in the compound of formula (II) and $R_2$ in the compound of formula (III) is —$CH_2OP$.

In one embodiment, Y is —$SO_2NH_2$ and $Y_1$ is —H in the compound of formula (II) and $R_2$ in the compound of formula (III) is —$CH_2F$.

When $R_2$ is —$CH_2OP$, the protecting group, P, can be removed in the compound of formula (I) to provide the compound of formula (I) wherein $R_2$ is —$CH_2OH$. The protecting group, P, can be removed using methods well known to those skilled in the art (See, e.g., T. W. Greene, Protective Groups in Organic Synthesis, John Wiley-Interscience Publication, New York, (1981)). In one embodiment, the protecting group is an ester or an ether. In one embodiment, the protecting group is an acetate group.

The compound of formula (III) can be obtained by converting an N-trifluoroacetyl amino acid of formula (IV):

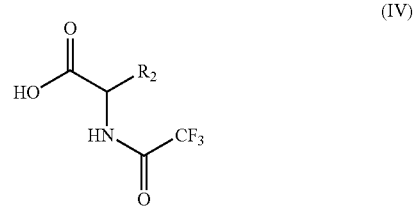

(IV)

wherein $R_2$ is —$CH_3$, —$CH_2F$, or —$CH_2OP$ and P is a hydroxyl protecting group, to an acid halide.

In one embodiment, $R_2$ in the compound of formula (IV) is —$CH_2OP$ and —P is —$C(O)CH_3$.

Acid halides can be obtained from carboxylic acids using methods well known to those skilled in the art, such as those described in J. March, *Advanced Organic Chemistry, Reaction Mechanism and Structure*, 4$^{th}$ ed. John Wiley & Sons, NY 1992, pp. 437-8. For example, acid halides can be obtained by reacting carboxylic acids with thionyl chloride, bromide, or iodide. Acid chlorides or bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride.

The N-trifluoroacetyl amino acid of formula (IV) can be obtained by reacting an (L) amino acid of formula (V):

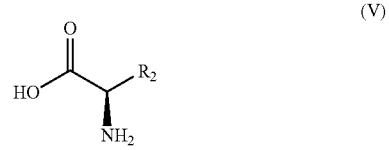

(V)

wherein $R_2$ has the meaning described above, with a trifluoroacetyl halide, preferably trifluoroacetyl chloride, or trifluoracetic anhydride to provide an N-trifluoracetylated amino acid of formula (IV) using methods well known to those skilled in the art (See, e.g., in J. March, *Advanced Organic Chemistry, Reaction Mechanism and Structure*, 4$^{th}$ ed. John Wiley & Sons, NY 1992, pp. 417-419).

In one embodiment, $R_2$ is —$CH_3$. When $R_2$ is —$CH_3$, the amino acid of formula (V) is (L) alanine. (L) alanine is a naturally occurring amino acid and is commercially available.

In one embodiment, $R_2$ is —$CH_2OH$. When $R_2$ is —$CH_2OH$, the amino acid of formula (V) is (L) serine. (L) serine is a naturally occurring amino acid and is commercially available.

In one embodiment, $R_2$ is —$CH_2F$. The amino acid of formula (V), wherein $R_2$ is —$CH_2F$, can be readily obtained by fluorinating the hydroxyl of serine using methods well known to those skilled in the art (See, e.g., in J. March, *Advanced Organic Chemistry, Reaction Mechanism and Structure*, 4$^{th}$ ed. John Wiley & Sons, NY 1992, pp. 431-433, see also, J. Yin et al., *Organic Letters*, 6:9 (2004) 1465-1468).

Representative reagents for converting the hydroxyl of serine to a fluoride include, but are not limited to, diethylaminosulfur trifluoride ($(CH_3CH_2)_2NSF_3$, DAST); NaF, KF, or $NH_4F$ in polyhydrogen-fluoride-pyridine solution; and triethylamine trihydrofluoride and perfluoro-1-butanesulfonyl fluoride.

In one embodiment, $R_2$ is $-CH_2OP$. The amino acid of formula (V), wherein $R_2$ is $-CH_2OP$, can be readily obtained by simply protecting the hydroxyl of serine using methods well known to those skilled in the art (See, e.g., T. W. Greene, Protective Groups in Organic Synthesis, John Wiley-Interscience Publication, New York, (1981)). As one of ordinary skill in the art would readily recognize it may be necessary to protect the nitrogen of serine before the hydroxyl of the serine is protected with the oxygen protecting group P.

In one embodiment, $R_2$ in the compound of formula (V) is $-CH_2OP$ and $-P$ is $-C(O)CH_3$. The compound of formula (V) wherein $R_2$ is $-CH_2OP$ and $-P$ is $-C(O)CH_3$ can be obtained by simply reacting serine with acetyl chloride. The compound of formula (V) wherein $R_2$ is $-CH_2OP$ and $-P$ is $-C(O)CH_3$, i.e., O-acetyl serine, is commercially available from Aldrich Chemical Co. of Milwaukee, Wis. as the hydrochloride salt. In one embodiment, $R_2$ in the compound of formula (V) is $-CH_2OP$ and $-P$ is $-C(O)CF_3$.

Although (L) alanine and (L) serine are the preferred amino acids, one of ordinary skill in the art will readily recognize that the above method could use (D) alanine and (D) serine or, for that matter, any (L) amino acid or any (D) amino acid.

One of ordinary skill in the art will readily recognize that functional groups in the compound of formula (II), i.e., Y and $Y_1$, may have to be protected during the synthesis of the compounds of formula (I). The functional groups in the compound of formula (II) can be readily protected, when required, using methods well known to those skilled in the art (See, e.g., T. W. Greene, Protective Groups in Organic Synthesis, John Wiley-Interscience Publication, New York, (1981)).

The compounds of formula (I) are useful for making fenicol antibiotics of general formula (VI):

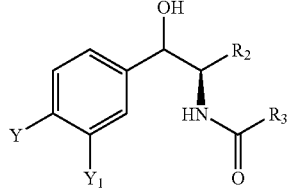

(VI)

wherein

Y, $Y_1$, $R_2$, and $R_3$ have the meaning provided above;

$R_3$ is a $-C_1-C_4$ hydrocarbon group, $-CH_2F$, $-CHF_2$, $-CF_3$, $-CH_2Cl$, $-CHCl_2$, $-CCl_3$, $-CH_2Br$, $-CHBr_2$, $-CBr_3$, $-CH_2I$, $-CHI_2$, $-CI_3$, $-CH_2CN$, $-CH_2N_3$, $-CH_2SO_2CH_3$, $-CZ_2CZ_3$, $-CH(CH_3)(CF_3)$, $-CH(OH)(CH_3)$, $-CH(CF_3)_2$, $-CH(CF_3)Z$, and $-CH(CF_3)OH$; and each Z is independently a hydrogen or halogen.

The fenicol compounds of formula (VI) are prepared by (i) reducing the carbonyl of the compound of formula (I) to provide a compound of formula (VII);

(ii) hydrolyzing the compound of formula (VII) to provide a compound of formula (VIII); and (iii) converting the compound of formula (VIII) to the fenicol compound of formula (VI).

The overall reaction scheme is depicted below:

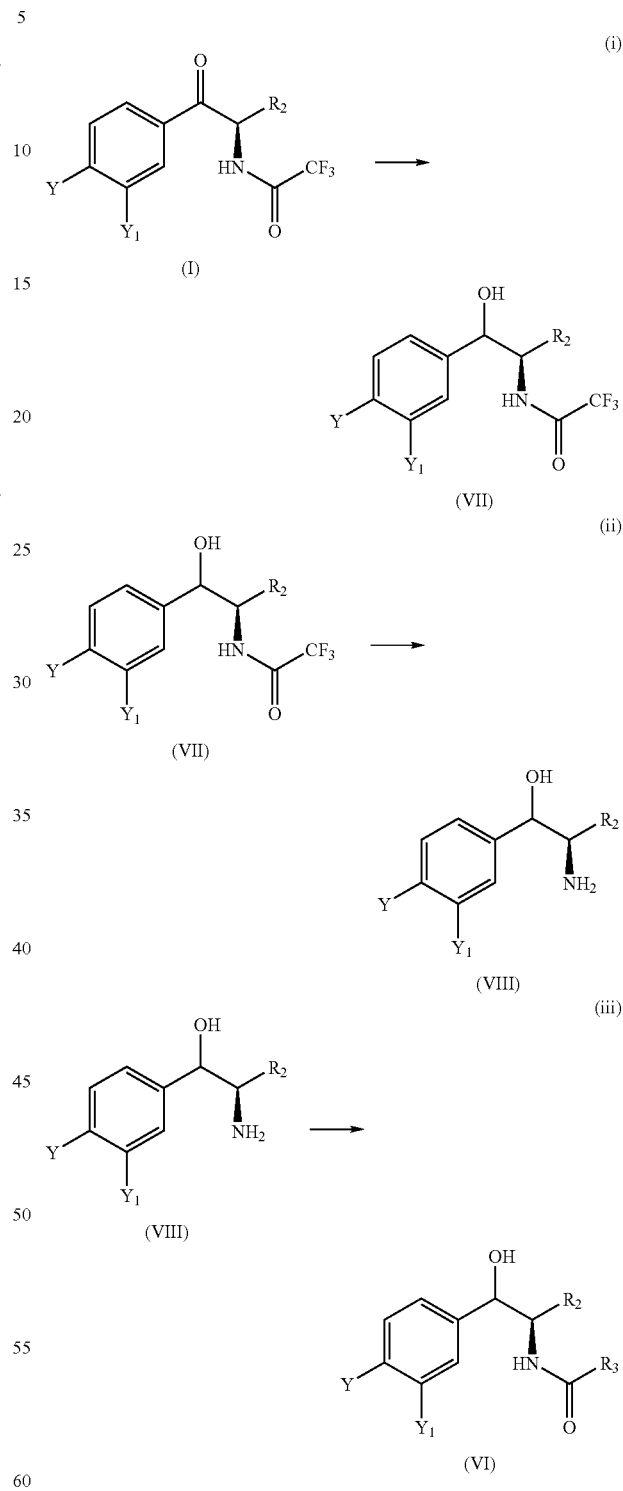

The carbonyl of the compound of formula (I) can be reduced, i.e., reaction (i), to provide the compound of formula (VII) using methods well known to those skilled in the art (See, e.g., in J. March, *Advanced Organic Chemistry, Reaction Mechanism and Structure*, 4$^{th}$ ed. John Wiley & Sons, NY 1992, pp. 910-918). Suitable reagents for reducing the carbonyl group include, but are not limited to sodium borohydride, lithium aluminum hydride, and diborane.

Reduction of the carbonyl of the compound of formula (I) to provide a compound of formula (VII) typically provides the compound of formula (VII) as a pair of diasteriomers, i.e., compounds of formula (VIIa) and (VIIb):

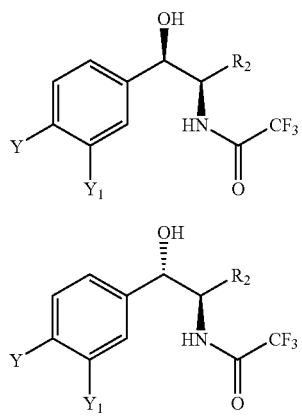

Optionally, diasteriomers (VIIa) and (VIIb) can be separated using methods well known to those skilled in the art including, but not limited to, recrystallization, column chromatography, preparative HPLC, and recrystallization to provide each diasteriomer substantially free of the other diasteriomer (See, for example, *Enantiomers, Racemates, and Resolution*, J. Jacques and S. Lutio, John Wiley & Sons 1981).

In one embodiment, the diasteriomer (VIIa) (or (VIIb)) is obtained wherein the amount of diasteriomer (VIIb) (or (VIIa)) is less than about 3 percent by weight of the combined amount of diasteriomer (VIIa) and (VIIb).

In one embodiment, the diasteriomer (VIIa) (or (VIIb)) is obtained wherein the amount of diasteriomer (VIIb) (or (VIIa)) is less than about 2 percent by weight of the combined amount of diasteriomer (VIIa) and (VIIb).

In one embodiment, the diasteriomer (VIIa) (or (VIIb)) is obtained wherein the amount of diasteriomer (VIIb) (or (VIIa)) is less than about 1 percent by weight of the combined amount of diasteriomer (VIIa) and (VIIb).

In one embodiment, the diasteriomer (VIIa) (or (VIIb)) is obtained wherein the amount of diasteriomer (VIIb) (or (VIIa)) is less than about 0.5 percent by weight of the combined amount of diasteriomer (VIIa) and (VIIb).

Each individual diasteriomer (VIIa) and (VIIb), substantially free of the other diasteriomer, can then be used in the subsequent step of the reaction to provide individual diasteriomers of formula (VIII), i.e., (VIIIa) and (VIIIb):

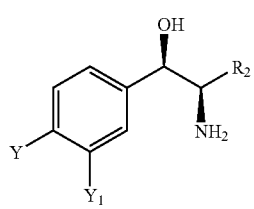

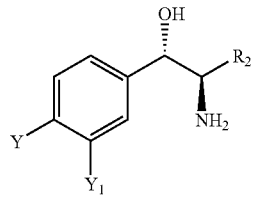

substantially free of the other diasteriomer.

Alternatively, a mixture of diasteriomers (VIIa) and (VIIb) can be used in the subsequent step of the reaction to provide a mixture of diasteriomers of formula (VIIIa) and (VIIIb), which can then be separated using methods well known to those skilled in the art including, but not limited to, those described above to provide each diasteriomer substantially free of the other diasteriomer.

In one embodiment, the diasteriomer (VIIIa) (or (VIIIb)) is obtained wherein the amount of diasteriomer (VIIIb) (or (VIIIa)) is less than about 3 percent by weight of the combined amount of diasteriomer (VIIIa) and (VIIIb).

In one embodiment, the diasteriomer (VIIIa) (or (VIIIb)) is obtained wherein the amount of diasteriomer (VIIIb) (or (VIIIa)) is less than about 2 percent by weight of the combined amount of diasteriomer (VIIIa) and (VIIIb).

In one embodiment, the diasteriomer (VIIIa) (or (VIIIb)) is obtained wherein the amount of diasteriomer (VIIIb) (or (VIIIa)) is less than about 1 percent by weight of the combined amount of diasteriomer (VIIIa) and (VIIIb).

In one embodiment, the diasteriomer (VIIIa) (or (VIIIb)) is obtained wherein the amount of diasteriomer (VIIIb) (or (VIIIa)) is less than about 0.5 percent by weight of the combined amount of diasteriomer (VIIIa) and (VIIIb).

Each individual diasteriomer (VIIIa) and (VIIIb), substantially free of the other diasteriomer, can then be used in the subsequent steps of the reaction to provide individual diasteriomers of formula (VI), i.e., (VIa) and (VIb):

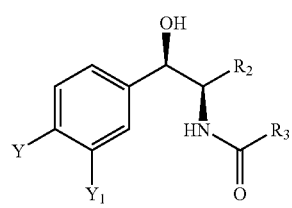

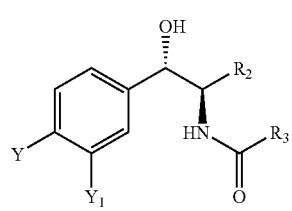

substantially free of the other diasteriomer.

Alternatively, a mixture of diasteriomers (VIIIa) and (VIIIb) can be used in the subsequent step of the reaction to provide a mixture of diasteriomers of formula (VIa) and (VIb), which can then be separated using methods well known to those skilled in the art including, but not limited to, those described above to provide each diasteriomer substantially free of the other diasteriomer.

In one embodiment, the diasteriomer (VIa) (or (VIb)) is obtained wherein the amount of diasteriomer (VIb) (or (VIa)) is less than about 3 percent by weight of the combined amount of diasteriomer (VIa) and (VIb).

In one embodiment, the diasteriomer (VIa) (or (VIb)) is obtained wherein the amount of diasteriomer (VIb) (or (VIa)) is less than about 2 percent by weight of the combined amount of diasteriomer (VIa) and (VIb).

In one embodiment, the diasteriomer (VIa) (or (VIb)) is obtained wherein the amount of diasteriomer (VIb) (or (VIa)) is less than about 1 percent by weight of the combined amount of diasteriomer (VIa) and (VIb).

In one embodiment, the diasteriomer (VIa) (or (VIb)) is obtained wherein the amount of diasteriomer (VIb) (or (VIa)) is less than about 0.5 percent by weight of the combined amount of diasteriomer (VIa) and (VIb).

In one embodiment, the carbonyl of the compound of formula (I) is reduced using a chiral reducing agent. Any chiral reducing agent known to one of ordinary skill in the art can be used in the methods of the invention. Representative chiral reducing agents include, but are not limited to, (R)- or (S)-β-isopinocampheyl-9-borabicyclo[3.3.1]nonane (Alpine-Borane) or (R)- or (S)-β-isopinocampheyl-9-borabicyclo[3.3.1] nonyl hydride (Alpine Hydride) (each commercially available from Aldrich Chemical Co., Milwaukee, Wis.) to provide a compound of formula (VII) as a single diasteriomer substantially free of the other diasteriomer, i.e., (VIIa) substantially free of (VIIb) or (VIIb) substantially free of (VIIa). Each individual diasteriomer (VIIIa) or (VIIIb) can then be used in the subsequent steps of the reaction to provide individual diasteriomers of formula (VI), i.e., (VIa) or (VIb).

The compound of formula (VII) or the individual diasteriomers of the compound of formula (VII), i.e., (VIIa) and (VIIb), can be hydrolyzed to the compound of formula (VIII) under acidic or basic conditions using methods well known to those skilled in the art. For example, the compound of formula (VII) can be hydrolyzed to the compound of formula (VIII) by dissolving the compound of formula (VII) in methanol and water containing excess, typically between about 2 and 10 fold excess, $Na_2CO_3$ or $K_2CO_3$ and allowing the reaction mixture to reflux. Generally the hydrolysis reaction is complete after between about 5 h and 18 h.

The compounds of formula (VIII) or the individual diateriomers of the compound of formula (VIII), i.e., (VIIIa) and (VIIb), can be converted to the fenicol compound of formula (VI) by simply reacting the compound of formula (VIII) with an acid halide, such as an acid chloride, of formula $R_3C(O)X$, wherein $R_3$ and X have the meaning described above.

The acid halide of formula $R_3C(O)X$ can be obtained from a carboxylic acid of formula $R_3C(O)OH$ using methods well known to those skilled including, but not limited to, the methods of making acid halides described above. The carboxylic acids of formula $R_3C(O)OH$ are commercially available or can be made by methods well known to those skilled in the art.

Accordingly, the invention is further directed to a method of making a fenicol compound of formula (VI) from a compound of formula (I). In one embodiment, the compounds of formula (I) used to prepare the fenicol compound of formula (VI) is obtained according to the method of the invention.

The invention is further directed to a method of making a fenicol compound of formula (VIa) from a compound of formula (I). In one embodiment, the compounds of formula (I) used to prepare the fenicol compound of formula (VIa) is obtained according to the method of the invention.

The invention is further directed to a method of making a fenicol compound of formula (VIb) from a compound of formula (I). In one embodiment, the compounds of formula (I) used to prepare the fenicol compound of formula (VIb) is obtained according to the method of the invention.

Optionally, the hydroxyl group of the fenicol compound of formula (VI) can be acylated with an acyl group of formula —$C(O)R_4$ to provide a compound of formula (IX):

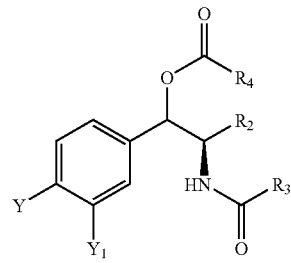

(IX)

wherein $R_4$ is a $C_1$ to $C_{18}$ hydrocarbon group that may be optionally substituted with a —$NH_2$ or a —COOH.

Similarly, the hydroxyl group of the individual diasteriomers of fenicol compound (VI), i.e., (VIa) and (VIb) can be acylated with an acyl group of formula —$C(O)R_4$ to provide compounds of formula (IXa) and (IXb), respectively.

The Fenicol Compounds of formula (IX) can be obtained by acylating the hydroxyl group of a Fenicol Compound of Formula (VI) using an acid halide of formula T-C(O)—$R_4$, wherein T is a halide, preferably chloride, and $R_4$ is as defined above, using methods well known to those skilled in the art. The Fenicol Compounds of formula (IX) can also be obtained by acylating the hydroxyl group of the Fenicol Compound of Formula (VI) with an acid anhydride using methods well known to those of ordinary skill in the art. Acid halides can be obtained using methods well known to those skilled in the art such as those described.

Illustrative Fenicol Compounds of Formula (VI) that can be prepared according to the method of the invention include, but are not limited to, those in Table I:

TABLE I

| Y | $Y_1$ | $R_2$ | $R_3$ |
|---|---|---|---|
| —$NO_2$ | —H | —$CH_3$ | —$CH_3$ |
| —$NO_2$ | —H | —$CH_3$ | —$CHCl_2$ |
| —$NO_2$ | —H | —$CH_3$ | —$CHF_2$ |
| —$NO_2$ | —H | —$CH_3$ | —$CH(CH_3)(CF_3)$ |
| —$NO_2$ | —H | —$CH_3$ | —$CH(CF_3)_2$ |
| —$NO_2$ | —H | —$CH_3$ | —$CH(CH_3)OH$ |
| —$NO_2$ | —H | —$CH_3$ | —$CH(CF_3)OH$ |
| —$NO_2$ | —H | —$CH_3$ | —$CH(CH_3)Cl$ |
| —$NO_2$ | —H | —$CH_3$ | —$CH(CH_3)Br$ |
| —$NO_2$ | —H | —$CH_3$ | —$CH(CH_3)I$ |
| —$NO_2$ | —H | —$CH_3$ | —$CH(CH_3)F$ |
| —$NO_2$ | —H | —$CH_3$ | —$CH(CF_3)Cl$ |
| —$NO_2$ | —H | —$CH_3$ | —$CH(CF_3)Br$ |
| —$NO_2$ | —H | —$CH_3$ | —$CH(CF_3)I$ |
| —$NO_2$ | —H | —$CH_3$ | —$CH(CF_3)F$ |
| —$NO_2$ | —H | —$CH_2OH$ | —$CH_3$ |
| —$NO_2$ | —H | —$CH_2OH$ | —$CHCl_2$ |
| —$NO_2$ | —H | —$CH_2OH$ | —$CHF_2$ |
| —$NO_2$ | —H | —$CH_2OH$ | —$CH(CH_3)(CF_3)$ |
| —$NO_2$ | —H | —$CH_2OH$ | —$CH(CF_3)_2$ |
| —$NO_2$ | —H | —$CH_2OH$ | —$CH(CH_3)OH$ |
| —$NO_2$ | —H | —$CH_2OH$ | —$CH(CF_3)OH$ |

TABLE I-continued

| Y | Y₁ | R₂ | R₃ |
|---|---|---|---|
| —NO₂ | —H | —CH₂OH | —CH(CH₃)Cl |
| —NO₂ | —H | —CH₂OH | —CH(CH₃)Br |
| —NO₂ | —H | —CH₂OH | —CH(CH₃)I |
| —NO₂ | —H | —CH₂OH | —CH(CH₃)F |
| —NO₂ | —H | —CH₂OH | —CH(CF₃)Cl |
| —NO₂ | —H | —CH₂OH | —CH(CF₃)Br |
| —NO₂ | —H | —CH₂OH | —CH(CF₃)I |
| —NO₂ | —H | —CH₂OH | —CH(CF₃)F |
| —NO₂ | —H | —CH₂OP | —CH₃ |
| —NO₂ | —H | —CH₂OP | —CHCl₂ |
| —NO₂ | —H | —CH₂OP | —CHF₂ |
| —NO₂ | —H | —CH₂OP | —CH(CH₃)(CF₃) |
| —NO₂ | —H | —CH₂OP | —CH(CF₃)₂ |
| —NO₂ | —H | —CH₂OP | —CH(CH₃)OH |
| —NO₂ | —H | —CH₂OP | —CH(CF₃)OH |
| —NO₂ | —H | —CH₂OP | —CH(CH₃)Cl |
| —NO₂ | —H | —CH₂OP | —CH(CH₃)Br |
| —NO₂ | —H | —CH₂OP | —CH(CH₃)I |
| —NO₂ | —H | —CH₂OP | —CH(CH₃)F |
| —NO₂ | —H | —CH₂OP | —CH(CF₃)Cl |
| —NO₂ | —H | —CH₂OP | —CH(CF₃)Br |
| —NO₂ | —H | —CH₂OP | —CH(CF₃)I |
| —NO₂ | —H | —CH₂OP | —CH(CF₃)F |
| —NO₂ | —H | —CH₂F | —CH₃ |
| —NO₂ | —H | —CH₂F | —CHCl₂ |
| —NO₂ | —H | —CH₂F | —CHF₂ |
| —NO₂ | —H | —CH₂F | —CH(CH₃)(CF₃) |
| —NO₂ | —H | —CH₂F | —CH(CF₃)₂ |
| —NO₂ | —H | —CH₂F | —CH(CH₃)OH |
| —NO₂ | —H | —CH₂F | —CH(CF₃)OH |
| —NO₂ | —H | —CH₂F | —CH(CH₃)Cl |
| —NO₂ | —H | —CH₂F | —CH(CH₃)Br |
| —NO₂ | —H | —CH₂F | —CH(CH₃)I |
| —NO₂ | —H | —CH₂F | —CH(CH₃)F |
| —NO₂ | —H | —CH₂F | —CH(CF₃)Cl |
| —NO₂ | —H | —CH₂F | —CH(CF₃)Br |
| —NO₂ | —H | —CH₂F | —CH(CF₃)I |
| —NO₂ | —H | —CH₂F | —CH(CF₃)F |
| —SO₂CH₃ | —H | —CH₃ | —CH₃ |
| —SO₂CH₃ | —H | —CH₃ | —CHCl₂ |
| —SO₂CH₃ | —H | —CH₃ | —CHF₂ |
| —SO₂CH₃ | —H | —CH₃ | —CH(CH₃)(CF₃) |
| —SO₂CH₃ | —H | —CH₃ | —CH(CF₃)₂ |
| —SO₂CH₃ | —H | —CH₃ | —CH(CH₃)OH |
| —SO₂CH₃ | —H | —CH₃ | —CH(CF₃)OH |
| —SO₂CH₃ | —H | —CH₃ | —CH(CH₃)Cl |
| —SO₂CH₃ | —H | —CH₃ | —CH(CH₃)Br |
| —SO₂CH₃ | —H | —CH₃ | —CH(CH₃)I |
| —SO₂CH₃ | —H | —CH₃ | —CH(CH₃)F |
| —SO₂CH₃ | —H | —CH₃ | —CH(CF₃)Cl |
| —SO₂CH₃ | —H | —CH₃ | —CH(CF₃)Br |
| —SO₂CH₃ | —H | —CH₃ | —CH(CF₃)I |
| —SO₂CH₃ | —H | —CH₃ | —CH(CF₃)F |
| —SO₂CH₃ | —H | —CH₂OH | —CH₃ |
| —SO₂CH₃ | —H | —CH₂OH | —CHCl₂ |
| —SO₂CH₃ | —H | —CH₂OH | —CHF₂ |
| —SO₂CH₃ | —H | —CH₂OH | —CH(CH₃)(CF₃) |
| —SO₂CH₃ | —H | —CH₂OH | —CH(CF₃)₂ |
| —SO₂CH₃ | —H | —CH₂OH | —CH(CH₃)OH |
| —SO₂CH₃ | —H | —CH₂OH | —CH(CF₃)OH |
| —SO₂CH₃ | —H | —CH₂OH | —CH(CH₃)Cl |
| —SO₂CH₃ | —H | —CH₂OH | —CH(CH₃)Br |
| —SO₂CH₃ | —H | —CH₂OH | —CH(CH₃)I |
| —SO₂CH₃ | —H | —CH₂OH | —CH(CH₃)F |
| —SO₂CH₃ | —H | —CH₂OH | —CH(CF₃)Cl |
| —SO₂CH₃ | —H | —CH₂OH | —CH(CF₃)Br |
| —SO₂CH₃ | —H | —CH₂OH | —CH(CF₃)I |
| —SO₂CH₃ | —H | —CH₂OH | —CH(CF₃)F |
| —SO₂CH₃ | —H | —CH₂OP | —CH₃ |
| —SO₂CH₃ | —H | —CH₂OP | —CHCl₂ |
| —SO₂CH₃ | —H | —CH₂OP | —CHF₂ |
| —SO₂CH₃ | —H | —CH₂OP | —CH(CH₃)(CF₃) |
| —SO₂CH₃ | —H | —CH₂OP | —CH(CF₃)₂ |
| —SO₂CH₃ | —H | —CH₂OP | —CH(CH₃)OH |
| —SO₂CH₃ | —H | —CH₂OP | —CH(CF₃)OH |
| —SO₂CH₃ | —H | —CH₂OP | —CH(CH₃)Cl |
| —SO₂CH₃ | —H | —CH₂OP | —CH(CH₃)Br |
| —SO₂CH₃ | —H | —CH₂OP | —CH(CH₃)I |
| —SO₂CH₃ | —H | —CH₂OP | —CH(CH₃)F |
| —SO₂CH₃ | —H | —CH₂OP | —CH(CF₃)Cl |
| —SO₂CH₃ | —H | —CH₂OP | —CH(CF₃)Br |
| —SO₂CH₃ | —H | —CH₂OP | —CH(CF₃)I |
| —SO₂CH₃ | —H | —CH₂OP | —CH(CF₃)F |
| —SO₂CH₃ | —H | —CH₂F | —CH₃ |
| —SO₂CH₃ | —H | —CH₂F | —CHCl₂ |
| —SO₂CH₃ | —H | —CH₂F | —CHF₂ |
| —SO₂CH₃ | —H | —CH₂F | —CH(CH₃)(CF₃) |
| —SO₂CH₃ | —H | —CH₂F | —CH(CF₃)₂ |
| —SO₂CH₃ | —H | —CH₂F | —CH(CH₃)OH |
| —SO₂CH₃ | —H | —CH₂F | —CH(CF₃)OH |
| —SO₂CH₃ | —H | —CH₂F | —CH(CH₃)Cl |
| —SO₂CH₃ | —H | —CH₂F | —CH(CH₃)Br |
| —SO₂CH₃ | —H | —CH₂F | —CH(CH₃)I |
| —SO₂CH₃ | —H | —CH₂F | —CH(CH₃)F |
| —SO₂CH₃ | —H | —CH₂F | —CH(CF₃)Cl |
| —SO₂CH₃ | —H | —CH₂F | —CH(CF₃)Br |
| —SO₂CH₃ | —H | —CH₂F | —CH(CF₃)I |
| —SO₂CH₃ | —H | —CH₂F | —CH(CF₃)F |
| —SO₂NH₂ | —H | —CH₃ | —CH₃ |
| —SO₂NH₂ | —H | —CH₃ | —CHCl₂ |
| —SO₂NH₂ | —H | —CH₃ | —CHF₂ |
| —SO₂NH₂ | —H | —CH₃ | —CH(CH₃)(CF₃) |
| —SO₂NH₂ | —H | —CH₃ | —CH(CF₃)₂ |
| —SO₂NH₂ | —H | —CH₃ | —CH(CH₃)OH |
| —SO₂NH₂ | —H | —CH₃ | —CH(CF₃)OH |
| —SO₂NH₂ | —H | —CH₃ | —CH(CH₃)Cl |
| —SO₂NH₂ | —H | —CH₃ | —CH(CH₃)Br |
| —SO₂NH₂ | —H | —CH₃ | —CH(CH₃)I |
| —SO₂NH₂ | —H | —CH₃ | —CH(CH₃)F |
| —SO₂NH₂ | —H | —CH₃ | —CH(CF₃)Cl |
| —SO₂NH₂ | —H | —CH₃ | —CH(CF₃)Br |
| —SO₂NH₂ | —H | —CH₃ | —CH(CF₃)I |
| —SO₂NH₂ | —H | —CH₃ | —CH(CF₃)F |
| —SO₂NH₂ | —H | —CH₂OH | —CH₃ |
| —SO₂NH₂ | —H | —CH₂OH | —CHCl₂ |
| —SO₂NH₂ | —H | —CH₂OH | —CHF₂ |
| —SO₂NH₂ | —H | —CH₂OH | —CH(CH₃)(CF₃) |
| —SO₂NH₂ | —H | —CH₂OH | —CH(CF₃)₂ |
| —SO₂NH₂ | —H | —CH₂OH | —CH(CH₃)OH |
| —SO₂NH₂ | —H | —CH₂OH | —CH(CF₃)OH |
| —SO₂NH₂ | —H | —CH₂OH | —CH(CH₃)Cl |
| —SO₂NH₂ | —H | —CH₂OH | —CH(CH₃)Br |
| —SO₂NH₂ | —H | —CH₂OH | —CH(CH₃)I |
| —SO₂NH₂ | —H | —CH₂OH | —CH(CH₃)F |
| —SO₂NH₂ | —H | —CH₂OH | —CH(CF₃)Cl |
| —SO₂NH₂ | —H | —CH₂OH | —CH(CF₃)Br |
| —SO₂NH₂ | —H | —CH₂OH | —CH(CF₃)I |
| —SO₂NH₂ | —H | —CH₂OH | —CH(CF₃)F |
| —SO₂NH₂ | —H | —CH₂OP | —CH₃ |
| —SO₂NH₂ | —H | —CH₂OP | —CHCl₂ |
| —SO₂NH₂ | —H | —CH₂OP | —CHF₂ |
| —SO₂NH₂ | —H | —CH₂OP | —CH(CH₃)(CF₃) |
| —SO₂NH₂ | —H | —CH₂OP | —CH(CF₃)₂ |
| —SO₂NH₂ | —H | —CH₂OP | —CH(CH₃)OH |
| —SO₂NH₂ | —H | —CH₂OP | —CH(CF₃)OH |
| —SO₂NH₂ | —H | —CH₂OP | —CH(CH₃)Cl |
| —SO₂NH₂ | —H | —CH₂OP | —CH(CH₃)Br |
| —SO₂NH₂ | —H | —CH₂OP | —CH(CH₃)I |
| —SO₂NH₂ | —H | —CH₂OP | —CH(CH₃)F |
| —SO₂NH₂ | —H | —CH₂OP | —CH(CF₃)Cl |
| —SO₂NH₂ | —H | —CH₂OP | —CH(CF₃)Br |
| —SO₂NH₂ | —H | —CH₂OP | —CH(CF₃)I |
| —SO₂NH₂ | —H | —CH₂OP | —CH(CF₃)F |
| —SO₂NH₂ | —H | —CH₂F | —CH₃ |
| —SO₂NH₂ | —H | —CH₂F | —CHCl₂ |
| —SO₂NH₂ | —H | —CH₂F | —CHF₂ |
| —SO₂NH₂ | —H | —CH₂F | —CH(CH₃)(CF₃) |
| —SO₂NH₂ | —H | —CH₂F | —CH(CF₃)₂ |
| —SO₂NH₂ | —H | —CH₂F | —CH(CH₃)OH |

TABLE I-continued

| Y | $Y_1$ | $R_2$ | $R_3$ |
|---|---|---|---|
| —SO$_2$NH$_2$ | —H | —CH$_2$F | —CH(CF$_3$)OH |
| —SO$_2$NH$_2$ | —H | —CH$_2$F | —CH(CH$_3$)Cl |
| —SO$_2$NH$_2$ | —H | —CH$_2$F | —CH(CH$_3$)Br |
| —SO$_2$NH$_2$ | —H | —CH$_2$F | —CH(CH$_3$)I |
| —SO$_2$NH$_2$ | —H | —CH$_2$F | —CH(CH$_3$)F |
| —SO$_2$NH$_2$ | —H | —CH$_2$F | —CH(CF$_3$)Cl |
| —SO$_2$NH$_2$ | —H | —CH$_2$F | —CH(CF$_3$)Br |
| —SO$_2$NH$_2$ | —H | —CH$_2$F | —CH(CF$_3$)I |
| —SO$_2$NH$_2$ | —H | —CH$_2$F | —CH(CF$_3$)F |

The invention further relates to a method of making a compound of formula (VIII) from a compound of formula (I). In one embodiment, the compounds of formula (I) used to prepare the compound of formula (VIII) is obtained according to the method of the invention.

The invention further relates to a method of making a compound of formula (VIIIa) from a compound of formula (I). In one embodiment, the compounds of formula (I) used to prepare the compound of formula (VIIIa) is obtained according to the method of the invention.

The invention further relates to a method of making a compound of formula (VIIIb) from a compound of formula (I). In one embodiment, the compounds of formula (I) used to prepare the compound of formula (VIIIb) is obtained according to the method of the invention.

The invention further relates to a method of making a compound of formula (VII) from a compound of formula (I). In one embodiment, the compounds of formula (I) used to prepare the compound of formula (VII) is obtained according to the method of the invention.

The invention further relates to a method of making a compound of formula (VIIa) from a compound of formula (I). In one embodiment, the compounds of formula (I) used to prepare the compound of formula (VIIa) is obtained according to the method of the invention.

The invention further relates to a method of making a compound of formula (VIIb) from a compound of formula (I). In one embodiment, the compounds of formula (I) used to prepare the compound of formula (VIIb) is obtained according to the method of the invention.

The invention further relates to a method of making a Fenicol Compound of formula (VI) from an amino acid of formula (V).

The invention further relates to a method of making a Fenicol Compound of formula (VIa) from an amino acid of formula (V).

The invention further relates to a method of making a Fenicol Compound of formula (VIb) from an amino acid of formula (V).

The invention further relates to a method of making a compound of formula (VII) from an amino acid of formula (V).

The invention further relates to a method of making a compound of formula (VIIa) from an amino acid of formula (V).

The invention further relates to a method of making a compound of formula (VIIb) from an amino acid of formula (V).

The invention further relates to a method of making a compound of formula (VIII) from an amino acid of formula (V).

The invention further relates to a method of making a compound of formula (VIIIa) from an amino acid of formula (V).

The invention further relates to a method of making a compound of formula (VIIIb) from an amino acid of formula (V).

The invention further relates to a method of making a fenicol compound of formula (VI) from an N-trifluoroacetyl amino acid of formula (IV).

The invention further relates to a method of making a fenicol compound of formula (VIa) from an N-trifluoroacetyl amino acid of formula (IV).

The invention further relates to a method of making a fenicol compound of formula (VIb) from an N-trifluoroacetyl amino acid of formula (IV).

The invention further relates to a method of making a compound of formula (VII) from an N-trifluoroacetyl amino acid of formula (IV).

The invention further relates to a method of making a compound of formula (VIIa) from an N-trifluoroacetyl amino acid of formula (IV).

The invention further relates to a method of making a compound of formula (VIIb) from an N-trifluoroacetyl amino acid of formula (IV).

The invention further relates to a method of making a compound of formula (VIII) from an N-trifluoroacetyl amino acid of formula (IV).

The invention further relates to a method of making a compound of formula (VIIIa) from an N-trifluoroacetyl amino acid of formula (IV).

The invention further relates to a method of making a compound of formula (VIIIb) from an N-trifluoroacetyl amino acid of formula (IV).

The invention further relates to a method of making a compound of formula (VI) from an N-trifluoroacetyl amino acid of formula (VII). In one embodiment, the compound of formula (VII) is prepared using the method of the invention.

The invention further relates to a method of making a compound of formula (VIa) from an N-trifluoroacetyl amino acid of formula (VII). In one embodiment, the compound of formula (VII) is prepared using the method of the invention.

The invention further relates to a method of making a compound of formula (VIb) from an N-trifluoroacetyl amino acid of formula (VII). In one embodiment, the compound of formula (VII) is prepared using the method of the invention.

The invention further relates to a method of making a compound of formula (VI) from an N-trifluoroacetyl amino acid of formula (VIII). In one embodiment, the compound of formula (VIII) is prepared using the method of the invention.

The invention further relates to a method of making a compound of formula (VIa) from an N-trifluoroacetyl amino acid of formula (VIII). In one embodiment, the compound of formula (VIII) is prepared using the method of the invention.

The invention further relates to a method of making a compound of formula (VIb) from an N-trifluoroacetyl amino acid of formula (VIII). In one embodiment, the compound of formula (VIII) is prepared using the method of the invention.

The invention further relates to a compound of formula (I).

The invention further relates to a compound of formula (VII).

The invention further relates to a fenicol compound of formula (VIa1):

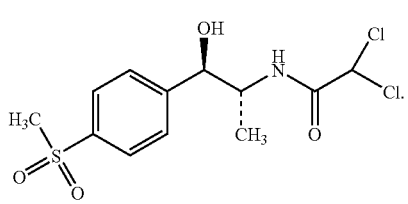

(VIa1)

The fenicol compound of formula (VIa1) can be made by the method of the invention starting with (L) alanine. The fenicol compound of formula (VIa1) is useful as an antibacterial agent. Accordingly, the invention further relates to a pharmaceutical composition comprising the fenicol compound of formula (VIa1) and a pharmaceutically acceptable excipient and to a method of preventing or treating a bacterial infection in an animal comprising administering to an animal in need thereof a fenicol compound of formula (VIa1).

When administered to an animal, the fenicol compound of formula (VIa1) is typically administered as a component of a composition that comprises a pharmaceutically acceptable carrier or excipient so as to provide the form for proper administration to the animal. The pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Suitable pharmaceutical excipients are described in *Remington's Pharmaceutical Sciences* 1447-1676 (Alfonso R. Gennaro ed., 19th ed. 1995), incorporated herein by reference.

In one embodiment, the fenicol compound of formula (VIa1) is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. Typically, the excipients are of pharmaceutical grade. Orally administered compositions can also contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used.

The fenicol compound of formula (VIa1) can also be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference.

Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the fenicol compound of formula (VIa1).

The invention thus encompasses single unit dosage forms suitable for oral administration such as, but not limited to, tablets, capsules, gelcaps, and caplets that are adapted for controlled- or sustained-release.

In another embodiment, the fenicol compound of formula (VIa1) is formulated for intravenous or parenteral administration. Typically, compositions for intravenous or parenteral administration comprise a suitable sterile solvent, which may be an isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the fenicol compound of formula (VIa1) is to be administered by infusion, it can be dispensed, for example, with an infusion bottle containing, for example, sterile pharmaceutical grade water or saline. Where the fenicol compound of formula (VIa1) is administered by injection, an ampule of sterile water for injection, saline, or other solvent can be provided so that the ingredients can be mixed prior to administration.

In one embodiment, the invention relates to methods of treating or preventing a condition in an animal comprising administering to an animal in need thereof an effective amount of a pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

The fenicol compound of formula (VIa1) can be administered by any convenient route, for example, by infusion or bolus injection, topically, by absorption through epithelial or mucocutaneous linings (e.g., oral, rectal, and intestinal mucosa, etc.), and can be administered together with another biologically active agent. Administration can be systemic or local. Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the fenicol compound of formula (VIa1) into the bloodstream.

In one embodiment, the pharmaceutical composition is administered orally.

In one embodiment, the pharmaceutical composition is administered topically.

In one embodiment, the pharmaceutical composition is administered by infusion or bolus injection.

In one embodiment, the animal is a mammal.

In one embodiment, the animal is a canine, a feline, an equine, a bovine, an ovine, or a porcine.

In one embodiment the animal is a human.

In one embodiment, the animal is a non-human animal.

In one embodiment, the animal is a dog.

In one embodiment, the animal is a cat.

In one embodiment, the animal is a cow.

In one embodiment, the animal is a pig.

In one embodiment, the animal is a horse.

In one embodiment, the animal is a sheep.

In one embodiment, the animal is a monkey.

In one embodiment, the animal is a baboon.

In one embodiment, the animal is a rat.

In one embodiment, the animal is a mouse.

In one embodiment, the animal is a guinea pig.

Representative conditions that can be treated or prevented with the methods of the invention include, but are not limited to, bacterial infections and nephrotic syndromes (such as those disclosed in U.S. Pat. No. 5,532,239, the contents of which are expressly incorporated herein by reference thereto).

In one embodiment, the condition is a bacterial infection.

In one embodiment, the condition is a bacterial infection caused by *Staphylococcus aureus, Streptococcus pneumoniae*, coagulese-negative staphylococci, *Streptococcus pyogenes, Staphylococcus epidermis, Pseudomonas aeruginosa, Escherichia coli, Klebsiella pneumoniae, Enterbacter cloacae, Proteus mirabilis, Proteus vulgaris, Providencia stuartii, Morganella morganii, Citrobacter diversus, Citrobacter freundii, Haemophilus influenzae*, or *Neisseria gonorrhea*.

In one embodiment, the condition is a respiratory tract infection, a urinary tract infection, a postoperative-wound infection, a bone or joint infection, a skin infection, an ear infection, or a sexually transmitted disease.

In one embodiment, the condition is a nephrotic syndrome.

The effective amount administered to the animal depends on a variety of factors including, but not limited to the type of animal being treated, the condition being treated, the severity of the condition, and the specific fluoroquinolone being administered. One of ordinary skill in the art will readily know what is an effective amount of the pharmaceutical composition to treat a condition in an animal.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Synthesis of D-(threo)-1-p-methylsulfonylphenyl-2-dichloroacetamido-1-propanol (Fenicol Compound (VIa1))

Thiamphenicol (1) (10.0 g, 28 mmol) was suspended in water containing 4 mL of concentrated hydrochloric acid and the resulting reaction mixture heated at reflux temperature for about 4 h. After heating, the solvent was removed under reduced pressure to provide a residue. Toluene (15 mL) was added to the resultant residue and the toluene evaporated.

Another 15 mL of toluene was then added to the residue and the toluene evaporated to provide a dry residue containing 1-para methyl sulfonylphenyl-2-amino-1,3-propanediol hydrochloride (2).

The 1-para methyl sulfonylphenyl-2-amino-1,3-propanediol hydrochloride (2) was added to 150 mL of a 1:1 mixture of 1,4-dioxane and saturated sodium bicarbonate solution. Di-tert-butyldicarbonate (7.65 g, 35 mmol) was then added and the resulting mixture was stirred for 48 hrs. The 1,4-dioxane was then removed under reduced pressure and the remaining liquid extracted with ethyl acetate (about 150 mL). The ethyl acetate layer was then washed with 0.1 N hydrochloric acid (about 10 mL), brine (about 10 mL), dried (Na$_2$SO$_4$), and concentrated to provide 8.63 g of a compound of formula 3.

The compound of formula 3 (1.0 g, 2.9 mmol) was dissolved in methylene chloride (15 ml) and pyridine (10 ml) was added to the solution. The solution was then cooled to 0° C. To the cooled solution was added a solution of p-toluene sulphonyl chloride in dichloromethane (5 mL) drop wise over a time period of about 15 min. The resulting reaction mixture was then allowed to stir at 0° C. for about 15 min. and then allowed to warm to about 25° C. over a time period of about 1 hr. The solvent was removed under reduced pressure to provide crude mono-tosylate (4) that was used for the next step without further purification.

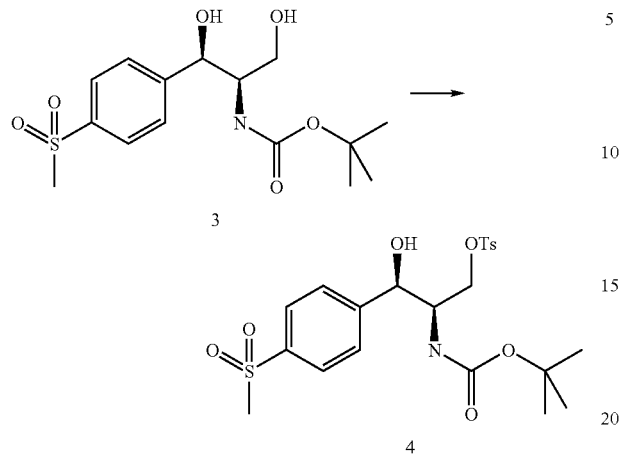

The mono-tosylate (4) was dissolved in tetrahydrofuran (15 mL) and the solution cooled to 0° C. To the cooled solution was added lithium aluminum hydride in 3 parts over a time period of about 15 min. The resulting reaction mixture was allowed to stir at 0° C. for about 15 min. and then allowed to warm to about 25° C. over a time period of about 1 hr. The reaction mixture was then cooled to 0° C. and 2 mL of water added followed by sufficient 0.5 N aqueous hydrochloric acid to provide a pH of about 5. The tetrahydrofuran was then removed under reduced pressure and the resulting liquid extracted with ethyl acetate (50 mL). The ethyl acetate was removed under reduced pressure to provide crude compound of formula 5 that was purified by column chromatography using a silica column and ethyl acetate/hexane in a ratio of 1:9 as eluent to provide 0.8 g (83%) of purified compound of formula 5.

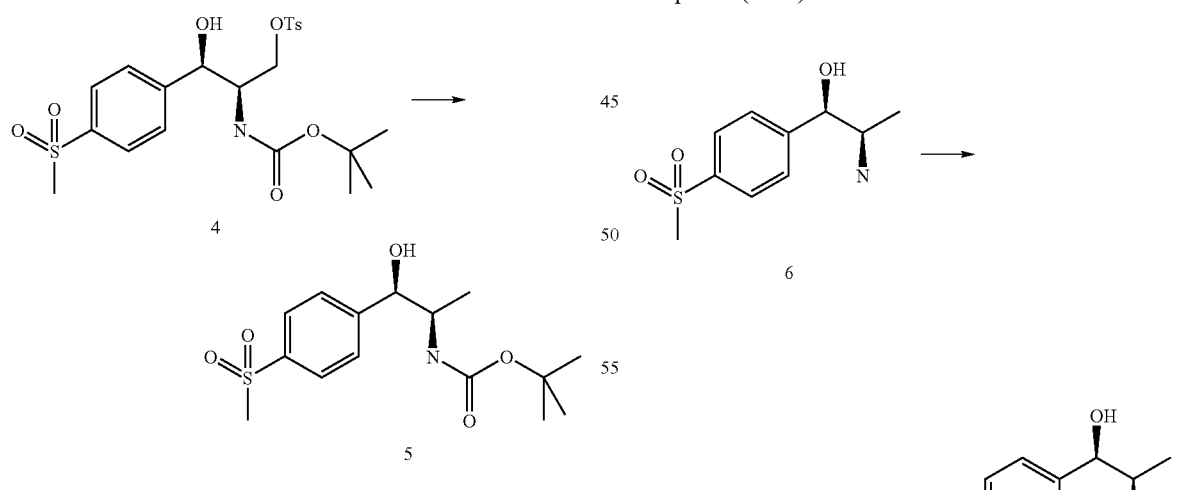

The compound of formula 5 (0.29 g, 0.88 mmol) was dissolved in methylene chloride (10 mL). To the resulting solution was then added 8 mL of trifluoroacetic acid at 25° C. The resulting solution was then stirred for about 2 hr. and the solvents removed under reduced pressure to provide a residue. The residue was dissolved in a 0.01 N aqueous sodium hydroxide solution (5 mL) and the resulting solution extracted twice with ethyl acetate (about 50 mL each extraction). The ethyl acetate solutions were combined, washed with brine (about 10 mL), dried (Na$_2$SO$_4$), and concentrated to provide 0.2 g of amine (6).

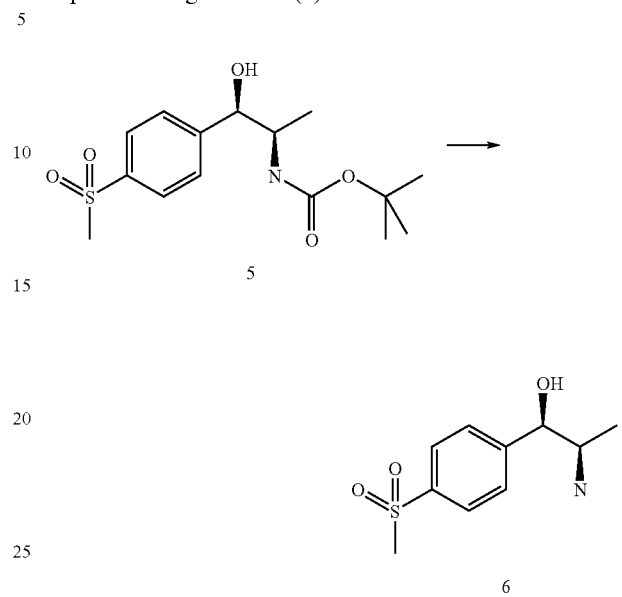

The amine (6) (0.2 g, 0.88 mmol) was dissolved in methylene chloride. To the resulting solution was added dichloroacetic anhydride (0.16 mL, 1.05 mmol) followed by triethylamine (0.5 mL). The reaction mixture was allowed to stir for about 90 min. and then was diluted to 25 mL with methylene chloride. The resulting solution washed with 1.0 N NaOH (about 10 mL), 1.0 N HCl (about 10 mL), and brine (about 10 mL); dried (Na$_2$SO$_4$); and concentrated under reduced pressure to provide crude compound of formula 7. Crude compound of formula 7 was purified by column chromatography using a silica gel column eluted with ethyl acetate/hexane in a ratio of 1:9 to provide 0.2 g (67%) of purified 7, i.e., fenicol compound (VIa1).

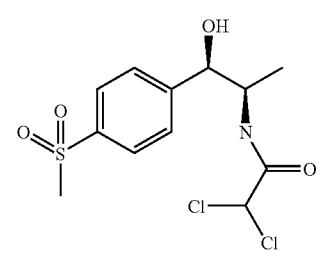

Example 2

Synthesis of D-(threo)-1-p-methylsulfonylphenyl-2-dichloroacetamido-1-propanol (Fenicol Compound (VIa1)) From L-Alanine Step 1: N-trifluoroacetyl Alanine L-Alanine (5.0 g, 5.6 mmol) was suspended in methylene chloride (20 mL) at 0° C. To the cooled solution was added trifluoroacetic anhydride (1.52 g, 7.3 mmol) with stirring. After the trifluoroacetic anhydride was added, the reaction mixture was allowed to warm to room temperature over a time period of about 30 min., with stirring, and stirring was continued for about 5 hrs. The solvent was then removed under reduced pressure and toluene (about 100 mL) was added. The toluene was distilled to remove water as an azeotrope and the remaining toluene removed under reduced pressure to provide N-(trifluoroacetyl)-L-alanine (90% yield).

Alternatively, N-trifluoroacetyl alanine can be prepared by suspending (2.0 g, 22 mmol) L-alanine in methanol (11 mL) and adding triethylamine (3.1 mL, 22 mmol) to the suspension with stirring. After stirring for about 5 min, ethyl trifluoroacetate (3.3 mL, 28 mmol) was added and the resulting mixture stirred for about 8 h at room temperature. The solvent was removed under reduced pressure and the resulting residue dissolved in water (50 mL), acidified with concentrated aqueous hydrochloric acid (4 mL), and stirred for about 15 min. The mixture was then extracted with ethyl acetate (2×30 mL) and the organic layers combined. The combined organic layers were then washed with brine (50 mL), dried ($Na_2SO_4$), and the ethyl acetate removed under reduced pressure to provide a solid which washed with n-hexane and dried to provide N-trifluoroacetyl alanine. (2.7 g, 86%, mp 68° C.; $^1$HNMR ($CDCl_3$) δ 1.58 (d, 3H, J=7.5 Hz), 4.68 (p, 1H, J=7.5 Hz), 6.87 (bs, 1H, NH)).

Step 2: S (−)-2-[N-(Trifluoroacetyl)amino]-1-(4-methylthiophenyl)-1-propanone

To a stirred mixture of N-(trifluoroacetyl)-L-alanine (5.05 g, 27.3 mmol) and pyridine (0.3 mL) was added oxalyl chloride (7.62 g, 60 mmol) at 0° C. under a nitrogen atmosphere. The reaction mixture was then allowed to warm to room temperature and stirred for an additional 2 hrs. The reaction mixture was then concentrated under reduced pressure to provide an oil that was combined with 8 mL of thioanisole. The resulting solution was then added a solution of $AlCl_3$ (76 mmol, about 2.8 eq. relative to the N-(trifluoroacetyl)-L-alanine, about 10 g) in thioanisole (7 mL) at 0° C. The resulting reaction mixture was then allowed to warm to room temperature and stirred for about 14 hrs. After stirring, the reaction mixture was poured into cold 1 N aqueous hydrochloric acid (200 mL) and the resulting mixture extracted with ethyl acetate (200 mL), the ethyl acetate dried ($Na_2SO_4$), and the ethyl acetate removed under reduced pressure to provide a residue that was purified by flash chromatography using a silica gel column eluted with ethyl acetate/hexane in a ratio of 1:9 to provide S (−)-2-[N-(trifluoroacetyl)amino]-1-(4-methylthiophenyl)-1-propanone (B) (35% yield).

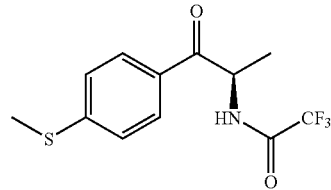

(B)

Step 3: Reduction of S (−)-2-[N-(Trifluoroacetyl)amino]-1-(4-methylthiophenyl)-1-propanone (B) to Provide Compound C To a stirred mixture of compound B (1.00 g, 3.44 mmol) in tetrahydrofuran (10 mL) was added 10.4 mL of 1.0M super hydride (lithium triethylborohydride in tetrahydrofuran, commercially available from Sigma-Aldrich of Milwaukee, Wis.) at −76° C. After 1 hr., 2 mL of water was added to the mixture followed by the slow addition of 30% $H_2O_2$ (5 mL) at −76° C. The tetrahydrofuran was then removed under reduced pressure and the resulting crude material was combined with ethyl acetate (100 mL). The resulting ethyl acetate solution washed with 1N aqueous hydrochloric acid (50 mL), saturated sodium bicarbonate (50 mL), and dried ($MgSO_4$). The ethyl acetate was then removed under reduced pressure to provide crude compound C. Compound C was purified by flash chromatography using a silica gel column eluted with hexane/ethyl acetate in a ratio of 1:9 to provide 100 mg (10% yield) of compound C.

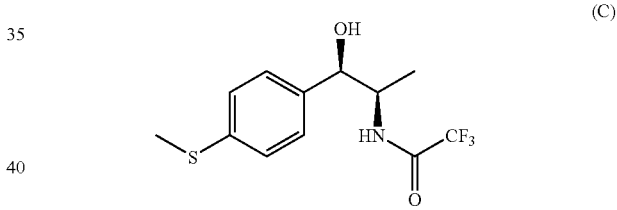

(C)

Step 4: Removal of the Trifluoroacetyl Group on Compound C and Formation of Dichloroacetamide D Compound C (60 mg, 0.2 mmol) was dissolved in methanol (5 mL). To the resulting methanol solution was added $K_2CO_3$ (113 mg, 0.8 mmol) in 2 mL of water. The resulting reaction mixture was then warmed to 60° C. for 18 hrs. The methanol was then removed under reduced pressure to provide a mixture that was extracted with ethyl acetate (about 25 mL). The ethyl acetate extract washed with brine (about 5 mL), dried ($Na_2SO_4$), and the ethyl acetate removed under reduced pressure. The resulting residue was dissolved in anhydrous tetrahydrofuran (2 mL) and cooled to 0° C. and dichloroacetic anhydride (60 mg, 0.25 mmol). was added to the cooled solution. The resulting solution was allowed to warm to room temperature and stirred for about 2 hrs. at room temperature. The tetrahydrofuran was removed under reduced pressure and the resulting residue dissolved in ethyl acetate (40 mL). The ethyl acetate solution was then washed with saturated sodium bicarbonate solution (about 5 mL) followed by brine (about 5 mL) and dried ($Na_2SO_4$). The ethyl acetate was then removed under reduced pressure to provide a residue that was purified using flash chromatography using silica gel and ethyl acetate/hexane in a ratio of 1:9 as eluent to provide compound D (yield 80%).

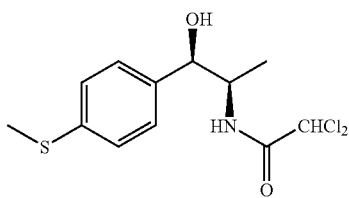

(D)

Step 5: Oxidation of the Sulfide Group of Compound D to Provide Sulfone E

Compound D (43 mg, 0.14 mmol) was dissolved in methanol (2 mL). To the resulting solution was added Oxone® (189 mg, 0.307 mmol) (commercially available from DuPont Specialty Chemicals of Wilmington, Del.) in 2 mL of water with stirring. The resulting solution was warmed to 60° C. and stirred for about 1 hr. The methanol was then removed under reduced pressure and ethyl acetate (50 mL) was added to the resulting residue. The resulting solution was then washed with water (about 5 mL) and brine (about 5 mL). The organic layer was then dried ($Na_2SO_4$) and the ethyl acetate removed under reduced pressure. The resulting residue was purified by flash chromatography using a silica gel column eluted with ethyl acetate/hexane in a ratio of 1:9 to provide D-(threo)-1-p-methylsulfonylphenyl-2-dichloroacetamido-1-propanol i.e., Fenicol Compound (VIa1) (90% yield).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference. Citation of any reference in this application, unless specifically identified as prior art, is not to be construed that such reference is prior art to the present application.

What is claimed is:

1. A method of synthesizing a fenicol compound of formula (VI):

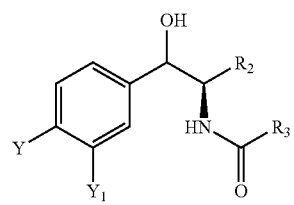

(VI)

wherein
each Y and $Y_1$ is independently —H; —$SO_2R_1$; —S(O)$R_1$—$SR_1$; —S(O)$NH_2$; —$SO_2NH_2$; —S(O)$NHR_1$; —S(O)$NHR_1$; —S(O)$N(R_1)_2$; —S(O)$N(R_1)_2$; —C(O)$R_1$; —C(O)$OR_1$; —OC(O)$R_1$; —$OR_1$; —$R_1$; —CN; halogen; —$NO_2$; —$NH_2$; —$NHR_1$; —$NH(R_1)_2$; —C(O)$NH_2$; —C(O)$NHR_1$; —C(O)$N(R_1)_2$; phenyl; or phenyl substituted with halogen; —$NO_2$, —$SO_2R_1$, —$OR_1$, or —$R_1$, each $R_1$ is independently a $C_1$-$C_4$ hydrocarbon group, $R_2$ is —$CH_3$, —$CH_2F$, or —$CH_2OP$, P is a hydroxyl protecting group, $R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —CH(OH)($CH_3$), —$CH(CF_3)_2$, —$CH(CF_3)Z$, and —$CH(CF_3)OH$; and each Z is independently a hydrogen or halogen, comprising the steps of:

(i) converting an amino acid of formula (V):

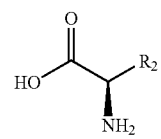

(V)

to a N-trifluoroacetylated amino acid of formula (IV):

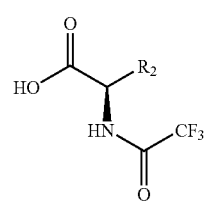

(IV)

(ii) converting the N-trifluoroacetylated amino acid of formula (IV) to a compound of formula (III):

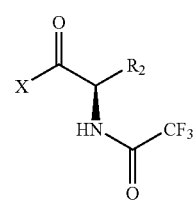

(III)

wherein X is a halide;

(iii) contacting the compound of formula (III) with a compound of formula (II):

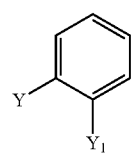

(II)

to provide a compound of formula (I):

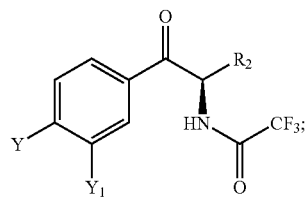

(iv) contacting the compound of formula (I) with a reducing agent to provide a compound of formula (VII):

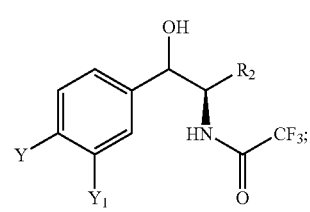

(v) converting the compound of formula (VII) to a compound of formula (VIII):

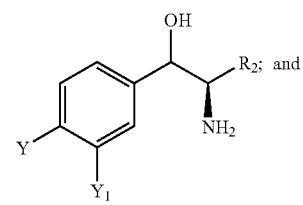

(vi) converting the compound of formula (VIII) to a compound of formula (VI).

2. The method of claim 1, wherein converting the compound of formula (VII) to a compound of formula (VIII) involves hydrolyzing the compound of formula (VII) under basic conditions.

3. The method of claim 2, wherein converting the compound of formula (VII) to a compound of formula (VIII) involves contacting the compound of formula (VII) an aqueous methanol solvent containing about a 2 to 10 fold molar excess of $Na_2CO_3$ or $K_2CO_3$ relative to the compound of formula (VII).

4. The method of claim 1, wherein $Y_1$ is hydrogen and Y is selected from the group consisting of $-NO_2$, $-SO_2CH_3$, and $-SO_2NH_2$.

5. The method of claim 1, wherein the compound of formula (II) is contacted with a compound of formula (III) in the presence of a Friedel-Crafts catalyst.

6. The method of claim 5, wherein the Friedel Crafts catalyst is selected from the group consisting of $AlCl_3$, $AlBr_3$, $BF_3$, $BCl_3$, $GaCl_3$, $FeCl_3$, $SbCl_5$, $ZrCl_4$, $SnCl_4$, $SbCl_3$, and $ZnCl_2$.

7. The method of claim 6, wherein the Friedel Crafts catalyst is present in an amount ranging from about 0.1 molar equivalents to 3 molar equivalents relative to the compound of formula (III).

8. The method of claim 1, wherein the amino acid of formula (V) is converted to the N-trifluoroacetylated amino acid of formula (IV) by contacting the amino acid of formula (V) with trifluoroacetic anhydride or trifluoroacetyl chloride.

9. The method of claim 1, wherein the reducing agent is a chiral reducing agent.

10. The method of claim 1, wherein the fenicol compound of formula (VI) is a compound of formula (VIa):

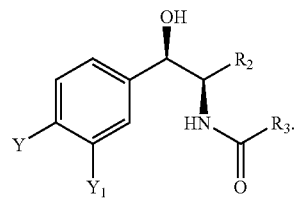

11. The method of claim 1, wherein the compound of formula (VII) is a compound of formula (VIIa):

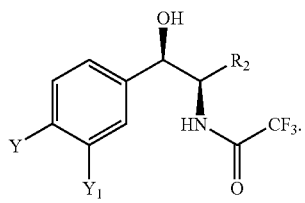

12. The method of claim 1, wherein the compound of formula (VIII) is a compound of formula (VIIIa):

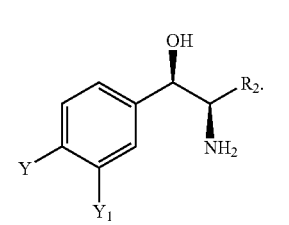

13. A method of synthesizing a fenicol compound of formula (VI):

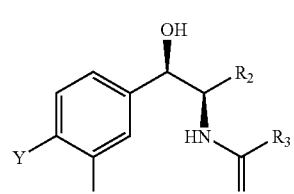

wherein each Y and $Y_1$ is independently —H; —$SO_2R_1$; —$S(O)R_1$—$SR_1$; —$S(O)NH_2$; —$SO_2NH_2$; —$S(O)NHR_1$; —$S(O)NHR_1$; —$S(O)N(R_1)_2$; —$S(O)N(R_1)_2$; —$C(O)R_1$; —$C(O)OR_1$; —$OC(O)R_1$; —$OR_1$; —$R_1$; —CN; halogen; —$NO_2$; —$NH_2$; —$NHR_1$; —$NH(R_1)_2$; —$C(O)NH_2$; —$C(O)NHR_1$; —$C(O)N(R_1)_2$; phenyl; or phenyl substituted with halogen; —$NO_2$, —$SO_2R_1$, —$OR_1$, or —$R_1$, each $R_1$ is independently a $C_1$-$C_4$ hydrocarbon group, $R_2$ is —$CH_3$, —$CH_2F$, or —$CH_2OP$, P is a hydroxyl protecting group, $R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —$CH(OH)(CH_3)$, —$CH(CF_3)_2$, —$CH(CF_3)Z$, and —$CH(CF_3)OH$; and each Z is independently a hydrogen or halogen, comprising the steps of:

(i) contacting a compound of formula (III):

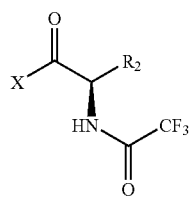

(III)

wherein:

$R_2$ is —$CH_3$, —$CH_2F$, or —$CH_2OP$,

P is a hydroxyl protecting group, and

X is a halide;

with a compound of formula (II):

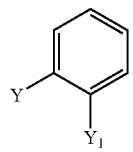

(II)

to provide a compound of formula (I):

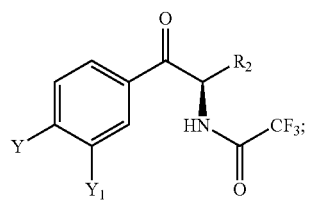

(I)

(ii) contacting the compound of formula (I) with a reducing agent to provide a compound of formula (VII):

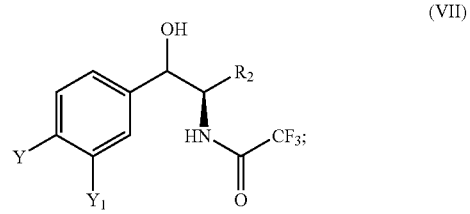

(VII)

(iii) converting the compound of formula (VII) to a compound of formula (VIII):

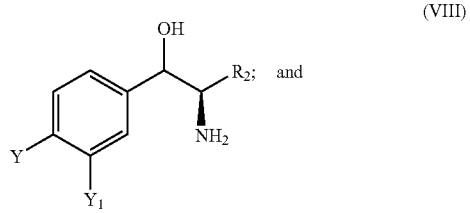

(VIII)

(iv) converting the compound of formula (VIII) to a compound of formula (VI).

14. The method of claim 13, wherein Y is selected from the group consisting of —$NO_2$, —$SO_2CH_3$, and —$SO_2NH_2$.

15. The method of claim 13, wherein the compound of formula (III) is contacted with a compound of formula (II) in the presence of a Friedel-Crafts catalyst.

16. The method of claim 15, wherein the Friedel Crafts catalyst is selected from the group consisting of $AlCl_3$, $AlBr_3$, $BF_3$, $BCl_3$, $GaCl_3$, $FeCl_3$, $SbCl_5$, $ZrCl_4$, $SnCl_4$, $SbCl_3$, and $ZnCl_2$.

17. The method of claim 16, wherein the Friedel Crafts catalyst is present in an amount ranging from about 0.1 molar equivalents to 3 molar equivalents relative to the compound of formula (III).

18. The method of claim 13, wherein the reducing agent is a chiral reducing agent.

19. The method of claim 13, wherein the fenicol compound of formula (VI) is a compound of formula (VIa):

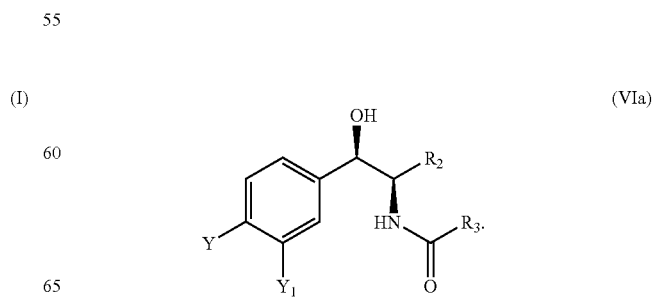

(VIa)

20. The method of claim 13, wherein the compound of formula (VII) is a compound of formula (VIIa):

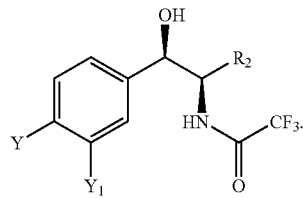
(VIIa)

21. The method of claim 13, wherein the compound of formula (VIII) is a compound of formula (VIIIa):

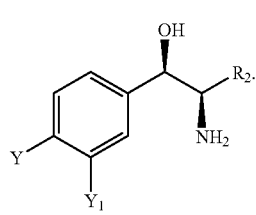
(VIIIa)

22. A method of synthesizing a fenicol compound of formula (VI):

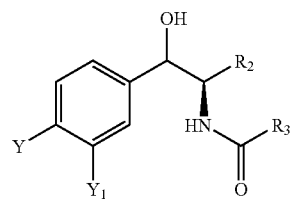
(VI)

wherein:
each Y and $Y_1$ is independently —H; —$SO_2R_1$; —$S(O)R_1$—$SR_1$; —$S(O)NH_2$; —$SO_2NH_2$; —$S(O)NHR_1$; —$S(O)NHR_1$; —$S(O)N(R_1)_2$; —$S(O)N(R_1)_2$; —$C(O)R_1$; —$C(O)OR_1$; —$OC(O)R_1$; —$OR_1$; —$R_1$; —CN; halogen; —$NO_2$; —$NH_2$; —$NHR_1$; —$NH(R_1)_2$; —$C(O)NH_2$; —$C(O)NHR_1$; —$C(O)N(R_1)_2$; phenyl; or phenyl substituted with halogen; —$NO_2$, —$SO_2R_1$, —$OR_1$, or —$R_1$, each $R_1$ is independently a $C_1$-$C_4$ hydrocarbon group,
$R_2$ is —$CH_3$, —$CH_2F$, or —$CH_2OP$,
P is a hydroxyl protecting group,
$R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —$CH(OH)(CH_3)$, —$CH(CF_3)_2$, —$CH(CF_3)Z$, and —$CH(CF_3)OH$; and each Z is independently a hydrogen or halogen, comprising the step of (i) converting an amino acid of formula (V):

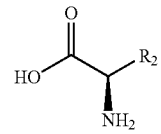
(V)

to a N-trifluoroacetylated amino acid of formula (IV):

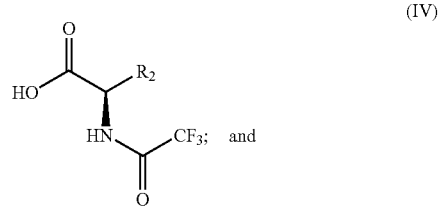
(IV)

(ii) converting the compound of formula (IV) to a compound of formula (VI).

23. A method of synthesizing a fenicol compound of formula (VI):

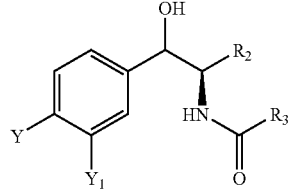
(VI)

wherein:
each Y and $Y_1$ is independently —H; —$SO_2R_1$; —$S(O)R_1$—$SR_1$; —$S(O)NH_2$; —$SO_2NH_2$; —$S(O)NHR_1$; —$S(O)NHR_1$; —$S(O)N(R_1)_2$; —$S(O)N(R_1)_2$; —$C(O)R_1$; —$C(O)OR_1$; —$OC(O)R_1$; —$OR_1$; —$R_1$; —CN; halogen; —$NO_2$; —$NH_2$; —$NHR_1$; —$NH(R_1)_2$; —$C(O)NH_2$; —$C(O)NHR_1$; —$C(O)N(R_1)_2$; phenyl; or phenyl substituted with halogen; —$NO_2$, —$SO_2R_1$, —$OR_1$, or —$R_1$, each $R_1$ is independently a $C_1$-$C_4$ hydrocarbon group,
$R_2$ is —$CH_3$, —$CH_2F$, or —$CH_2OP$,
P is a hydroxyl protecting group,
$R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —$CH(OH)(CH_3)$, —$CH(CF_3)_2$, —$CH(CF_3)Z$, and —$CH(CF_3)OH$; and each Z is independently a hydrogen or halogen,
comprising the step of
(i) contacting a compound of formula (III):

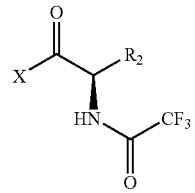

(III)

wherein X is a halide;
with a compound of formula (II):

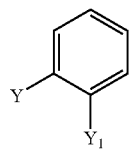

(II)

to provide a compound of formula (I):

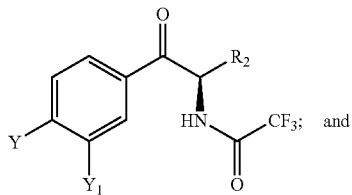

(I)

(ii) converting the compound of formula (I) to a compound of formula (VI).

24. A method of synthesizing a fenicol compound of formula (VI):

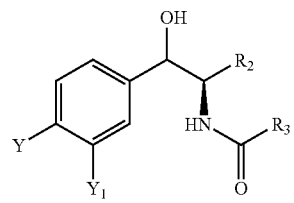

(VI)

wherein:
each Y and $Y_1$ is independently —H; —$SO_2R_1$; —S(O)$R_1$; —$SR_1$; —S(O)$NH_2$; —$SO_2NH_2$; —S(O)$NHR_1$; —S(O)$NHR_1$; —S(O)$N(R_1)_2$; —S(O)$N(R_1)_2$; —C(O)$R_1$; —C(O)$OR_1$; —OC(O)$R_1$; —$OR_1$; —$R_1$; —CN; halogen; —$NO_2$; —$NH_2$; —$NHR_1$; —$NH(R_1)_2$; —C(O)$NH_2$; —C(O)$NHR_1$; —C(O)$N(R_1)_2$; phenyl; or phenyl substituted with halogen; —$NO_2$, —$SO_2R_1$, —$OR_1$, or —$R_1$,
each $R_1$ is independently a $C_1$-$C_4$ hydrocarbon group,
$R_2$ is —$CH_3$, —$CH_2F$, or —$CH_2OP$,
P is a hydroxyl protecting group, $R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)$ ($CF_3$), —$CH(OH)(CH_3)$, —$CH(CF_3)_2$, —$CH(CF_3)Z$, and —$CH(CF_3)OH$; and
each Z is independently a hydrogen or halogen,
comprising the step of
(i) contacting a compound of formula (I):

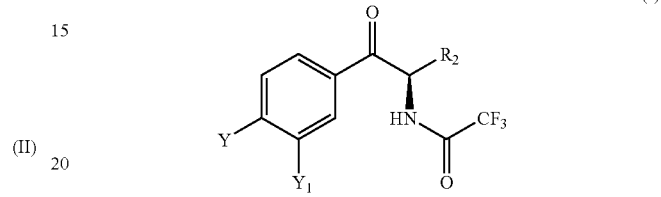

(I)

with a reducing agent to provide a compound of formula (VII):

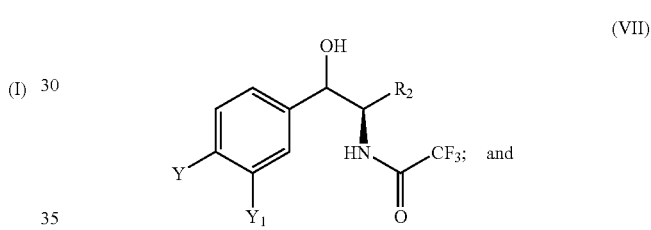

(VII)

(ii) converting the compound of formula (VII) to a compound of formula (VI).

25. The method of claim 24, wherein the reducing agent is a chiral reducing agent.

26. A method of synthesizing a fenicol compound of formula (VI):

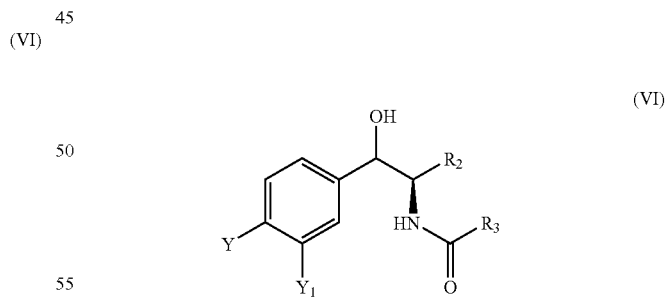

(VI)

wherein:
each Y and $Y_1$ is independently —H; —$SO_2R_1$; —S(O)$R_1$—$SR_1$; —S(O)$NH_2$; —$SO_2NH_2$; —S(O)$NHR_1$; —S(O)$NHR_1$; —S(O)$N(R_1)_2$; —S(O)$N(R_1)_2$; —C(O)$R_1$; —C(O)$OR_1$; —OC(O)$R_1$; —$OR_1$; —$R_1$; —CN; halogen; —$NO_2$; —$NH_2$; —$NHR_1$; —$NH(R_1)_2$; —C(O)$NH_2$; —C(O)$NHR_1$; —C(O)$N(R_1)_2$; phenyl; or phenyl substituted with halogen; —$NO_2$, —$SO_2R_1$, —$OR_1$, or —$R_1$, each $R_1$ is independently a $C_1$-$C_4$ hydrocarbon group,
$R_2$ is —$CH_3$, —$CH_2F$, or —$CH_2OP$,
P is a hydroxyl protecting group,
$R_3$ is a —$C_1$-$C_4$ hydrocarbon group, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2I$, —$CHI_2$, —$CI_3$, —$CH_2CN$, —$CH_2N_3$, —$CH_2SO_2CH_3$, —$CZ_2CZ_3$, —$CH(CH_3)(CF_3)$, —$CH(OH)(CH_3)$, —$CH(CF_3)_2$, —$CH(CF_3)Z$, and —$CH(CF_3)OH$; and
each Z is independently a hydrogen or halogen, comprising the steps:
(i) of converting a compound of formula (VII):

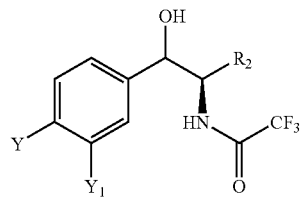

to a compound of formula (VIII):

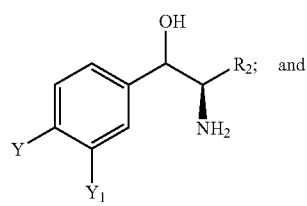

(ii) converting the compound of formula (VIII) to the fenicol compound of formula (VI).

27. The method of claim 26, wherein the compound of formula (VII) is a compound of formula (VIIa):

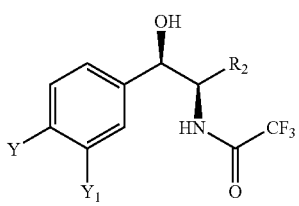

and the compound of formula (VIII) is a compound of formula (VIIIa):

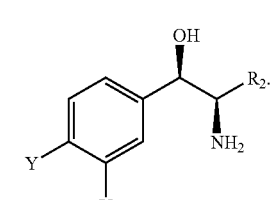

28. A method of synthesizing a compound of formula (I):

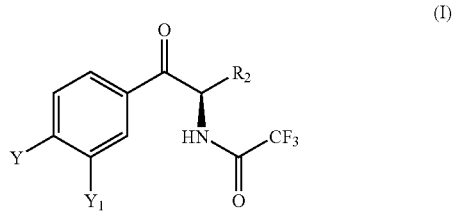

wherein:
each Y and $Y_1$ is independently —H; —$SO_2R_1$; —$S(O)R_1$—$SR_1$; —$S(O)NH_2$; —$SO_2NH_2$; —$S(O)NHR_1$; —$S(O)NHR_1$; —$S(O)N(R_1)_2$; —$S(O)N(R_1)_2$; —$C(O)R_1$; —$C(O)OR_1$; —$OC(O)R_1$; —$OR_1$; —$R_1$; —CN; halogen; —$NO_2$; —$NH_2$; —$NHR_1$; —$NH(R_1)_2$; —$C(O)NH_2$; —$C(O)NHR_1$; —$C(O)N(R_1)_2$; phenyl; or phenyl substituted with halogen; —$NO_2$, —$SO_2R_1$, —$OR_1$, or —$R_1$,
each $R_1$ is independently a $C_1$-$C_4$ hydrocarbon group,
$R_2$ is —$CH_3$, —$CH_2F$, or —$CH_2OP$,
P is a hydroxyl protecting group,
comprising contacting a compound of formula (II):

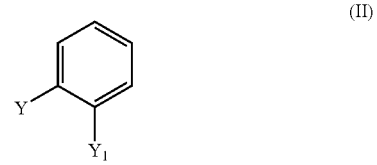

with a compound of formula (III):

wherein X is a halogen.

29. The method of claim 28, wherein Y is selected from the group consisting of —$NO_2$, —$SO_2CH_3$, and —$SO_2NH_2$.

30. The method of claim 28, wherein the compound of formula (I) is contacted with a compound of formula (II) in the presence of a Friedel-Crafts catalyst.

31. The method of claim 30, wherein the Friedel Crafts catalyst is selected from the group consisting of $AlCl_3$, $AlBr_3$, $BF_3$, $BCl_3$, $GaCl_3$, $FeCl_3$, $SbCl_5$, $ZrCl_4$, $SnCl_4$, $SbCl_3$, and $ZnCl_2$.

32. The method of claim 30, wherein the Friedel Crafts catalyst is present in an amount ranging from about 0.1 molar equivalents to 3 molar equivalents relative to the compound of formula (III).

33. A compound of formula (VIa1):

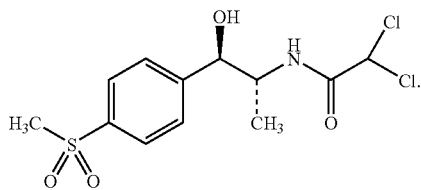

(VIa1)

34. A pharmaceutical composition comprising the compound of claim 33 and a pharmaceutically acceptable excipient.

35. A method of treating a condition selected from the group consisting of bacterial infections, nephritic syndromes, and sexually transmitted diseases that are responsive to administration of a compound of formula (VIa1) in an animal comprising administering to the animal the pharmaceutical composition of claim 34.

36. The method of claim 35, wherein the condition is a bacterial infection.

37. The method of claim 36, wherein the condition is a bacterial infection caused by *Staphylococcus aureus, Streptococcus pneumoniae*, coagulese-negative staphylococci, *Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii, Haemophilus influenzae*, or *Neisseria gonorrhea*.

38. The method of claim 35, wherein the condition is a respiratory tract infection, a urinary tract infection, a postoperative-wound infection, a bone or joint infection, a skin infection, an ear infection, or a sexually transmitted disease.

* * * * *